(12) United States Patent
Kamishita

(10) Patent No.: US 8,771,711 B2
(45) Date of Patent: Jul. 8, 2014

(54) SPRAYABLE GEL-TYPE SKIN/MUCOSA-ADHESIVE PREPARATION AND ADMINISTRATION SYSTEM USING THE PREPARATION

(75) Inventor: Taizou Kamishita, Osaka (JP)

(73) Assignee: Toko Yakuhin Kogyo Kabushiki Kaisha, Osaka (JP)

( * ) Notice: Subject to any disclaimer, the term of this patent is extended or adjusted under 35 U.S.C. 154(b) by 783 days.

(21) Appl. No.: 12/226,287

(22) PCT Filed: Apr. 20, 2007

(86) PCT No.: PCT/JP2007/058602
§ 371 (c)(1),
(2), (4) Date: Oct. 14, 2008

(87) PCT Pub. No.: WO2007/123193
PCT Pub. Date: Nov. 1, 2007

(65) Prior Publication Data
US 2009/0275668 A1     Nov. 5, 2009

(30) Foreign Application Priority Data

Apr. 21, 2006   (JP) ................................. 2006-118192

(51) Int. Cl.
*A61K 9/00*     (2006.01)
(52) U.S. Cl.
USPC ........................................................ 424/400
(58) Field of Classification Search
None
See application file for complete search history.

(56) References Cited

U.S. PATENT DOCUMENTS

| | | | |
|---|---|---|---|
| 5,000,355 A | 3/1991 | Pritchard | |
| 5,052,592 A | 10/1991 | Wilken et al. | |
| 5,125,539 A | 6/1992 | Schneider | |
| 5,158,761 A * | 10/1992 | Kamishita et al. | 424/45 |
| 5,215,739 A | 6/1993 | Kamishita et al. | |
| 5,782,345 A | 7/1998 | Guasch et al. | |
| 5,862,955 A | 1/1999 | Albini et al. | |
| 6,342,251 B1 | 1/2002 | Illum et al. | |
| 6,596,704 B1 * | 7/2003 | Court et al. | 514/54 |
| 7,306,123 B2 | 12/2007 | Masuda | |
| 8,136,703 B2 | 3/2012 | Kamishita | |
| 2001/0046519 A1 | 11/2001 | Illum et al. | |
| 2003/0073676 A1 * | 4/2003 | Biggadike et al. | 514/179 |
| 2003/0230600 A1 | 12/2003 | Masuda | |

FOREIGN PATENT DOCUMENTS

| | | |
|---|---|---|
| CA | 2 312 839 | 6/1999 |
| CA | 2 648 854 | 11/2007 |
| EP | 0 985 410 | 3/2000 |

(Continued)

OTHER PUBLICATIONS

Datta et al. "Development of a new nasal drug delivery system of diazepam with natural mucoadhesive agent from *Trigonella foenum-graecum* L". *Journal of Scientific and Industrial Research*, vol. 64, pp. 973-977 (2005).

(Continued)

*Primary Examiner* — Carlos Azpuru
*Assistant Examiner* — Casey Hagopian
(74) *Attorney, Agent, or Firm* — Hamre, Schumann, Mueller & Larson, P.C.

(57) ABSTRACT

The present invention provides a sprayable gel-type skin/mucosa-adhesive preparation comprising a gel formulation which contains an active pharmaceutical ingredient in a gel base material comprising a skin/mucosa-adhesive agent and an administration system comprising the preparation.

12 Claims, 9 Drawing Sheets

(56) References Cited

FOREIGN PATENT DOCUMENTS

| | | |
|---|---|---|
| JP | 59-55920 | 4/1984 |
| JP | 2-264714 | 10/1990 |
| JP | 6-23094 | 3/1994 |
| JP | 2001-89359 | 4/2001 |
| JP | 2003-212262 | 7/2003 |
| JP | 2004-99591 | 4/2004 |
| JP | 2004-189731 | 7/2004 |
| JP | 2004-238372 | 8/2004 |
| JP | 2005-104966 | 4/2005 |
| JP | 2006-44710 | 2/2006 |
| JP | 2006-83081 | 3/2006 |
| JP | 2008-44649 | 2/2008 |
| RU | 2 157 682 | 10/2000 |
| WO | WO 99/34776 | 7/1999 |
| WO | WO 2004/064867 | 8/2004 |

OTHER PUBLICATIONS

Co-pending U.S. Appl. No. 12/226,298 entitled fluid container and airless fluid dispensing system filed Oct. 14, 2008.

* cited by examiner

SPRAYABLE GEL-TYPE SKIN/MUCOSA-ADHESIVE PREPARATION AND ADMINISTRATION SYSTEM USING THE PREPARATION

TECHNICAL FIELD

The present invention relates to a gel-type skin/mucosa-adhesive preparation comprising an active pharmaceutical ingredient, and an administration system of the viscous gel-type skin/mucosa-adhesive preparation comprising an active pharmaceutical ingredient using a spray container for a gel formulation (upper-pressure-relief airless-type spray container) wherein the administration direction of the spray container can be optionally set. Especially, the present invention relates to a preparation for nasal drop, and an administration system of the preparation using a nasal spray wherein the preparation can be intranasally sprayed, optionally setting the administration direction of the spray container, in order to disperse and hold the gel preparation in a broad area of nasal cavity.

BACKGROUND ART

Currently, as a method for administrating a medicament, it is often used to spray a liquid drug preparation put in a spray container, to a mucosa and skin of a lumen and body surface. Especially, a drug preparation for intranasal administration is often used. The medicaments used for this purpose had been limited to a regional use such as a treatment for rhinitis. However, these days such administration is getting some attention for the purpose of systemic action. Low-molecular medicaments for systemic action such as butorphanol and sumatriptan, and peptidic medicaments such as calcitonin and desmopressin have been already sold in the market as a drug preparation for intranasal administration, and furthermore a lot of new applications via intranasal administration have been tried to get some absorption-improvement or fast-act.

The merits of a drug preparation for spray-administration to mucosa, especially a drug preparation for intranasal administration include that (1) fast act of a drug is expected because of its rapid absorption, (2) it is possible to avoid the decomposition of a drug due to the first-pass in liver, (3) it is possible to avoid the decomposition of a drug due to gastric acid or gastrointestinal enzyme in gastrointestinal tract, (4) it is possible to reduce the dose of a drug because of its high bioavailability, (5) it is a noninvasive administration compared with injection, (6) a patient can treat himself/herself, (7) a drug can directly reach the blood circulation or central nervous system, etc., while the demerits of a drug preparation for intranasal administration include that (1) the dose of a drug which can be administered to nasal cavity is limited to 25-200 µL per one operation, (2) a compound having a high molecular weight of 1 kD or more is hard to be absorbed via this route, (3) the absorption of a drug might be affected by the pathological state of nasal cavity, (4) the state of nasal cavity is varied between individuals, (5) the elimination system by mucociliary clearance might affect the absorption of a drug, (6) intranasal enzyme barrier exists, (7) nasal mucosa might be irritated by a drug, etc.

Nasal cavity is a site which first gets in contact with the outside, as well as oral cavity, which have a very outstanding character about the foreign-material-removal and prophylaxis. The abnormal activation of these actions or the failure thereby can cause rhinitis, nasal allergy, etc. Especially, pollinosis (hay fever) is becoming a serious social problem. For the purpose of the treatment of these nose-localized diseases, a lot of nasal spray preparations containing a vasoconstrictor agent, an antiallergic drug, a steroid, etc. have been put on the market.

Recently, some nasal absorption-type preparations containing a bioactive peptide or a water-soluble peptide having a molecular weight of 1000-3000 have been put on the market. These water-soluble high-molecular medicaments are ineffectual via oral administration, but effective only via injection. However, nasal administration can arrive at high bioavailability of several % to several 10%. The main reason thereof is thought that the permeability of epithelial layer in nasal mucosa which is an absorption path for water-soluble high-molecular medicaments is even higher than that of gastrointestinal tract or other mucosa. Thus, a nasal absorption-type preparation containing a water-soluble high-molecular medicament which is expected as a systemically effective formulation, is thought to be very useful as a noninvasive formulation type instead of an injection formulation.

Recently, a nasal absorption-type preparation which can be expected to mitigate an acute pain has been researched/developed as a narcotic analgesic and a migraine drug, on the basis of the fact that the permeability of epithelial layer in nasal mucosa is superior to that of other mucosa. A nasal absorption-type preparation containing such a medicament having central nervous system effect can markedly contribute the improvement of a patient's QOL, because it is expected to exert the pharmacological action more rapidly than a preparation for oral administration and it is possible to be administered by patient itself. A nasal cavity has a NALT (nasal-associated lymphoid tissue) which is similar to a lymphoid tissue. These days, some drug preparations for intranasal administration comprising influenza vaccine, diphtheria vaccine, etc. have been researched/developed as a vaccine-administration route for airborne-infectible virus, because the nasal immunoresponsiveness is high. Thus, it is so expected that a drug preparation for intranasal administration would be developed on the basis of the anatomical/physiological property of nasal cavity. However, for the drug design thereof it is required to understand the anatomical/physiological property of nasal cavity and surrounding tissue thereof.

A drug preparation for intranasal administration needs creative strategies because the clearance from nasal cavity is high. The preparation types for nasal cavity which have been developed include an ointment preparation, a droplet preparation, a spray-type preparation, a powder preparation, etc. These preparations are designed/developed so that an active medicament should effectively exert its effect in nasal cavity or be absorbed via the nasal cavity, i.e., the intranasal dispersibility of the preparations should be enhanced or the intranasal retention (adhesive property) should be enhanced, in order that the contacting time between an active medicament and nasal mucosa may be lengthened (JP-B-2011069).

An ointment preparation for nasal cavity is not so sanitary because it is usually put on with a finger, and additionally it is difficult to administer a predetermined amount of an active medicament because it is impossible to let the medicament reach the mucosa of deep nasal cavity with a finger.

A droplet preparation has been the most simple preparation for nasal cavity, however, it is difficult to accurately apply a predetermined amount thereof and further the applied medicament is removed from nasal cavity to pharynx through the mucociliary clearance.

A spray-type preparation is more dispersible than a droplet preparation because a liquid preparation can be pumped up, nebulized and intranasally sprayed.

A powder preparation is useful at the time of using a medicament decomposable in a solution or when the retention in nasal cavity should be held. However, the intranasal administration of a powder preparation might sometimes bring about some uncomfortable feelings and disorder of mucosa, and it is difficult to design a preparation having uniform particles.

Amongst these drug preparations for intranasal administration, a spray-type preparation is the most common preparation type because of its simplicity and comfortable feeling. On a spray-type preparation, some trials to enhance the efficacy and the absorption of a medicament have carried out by widening the contacting area between a medicament and nasal mucosa, and -lengthening the contacting time thereof, i.e., improving the retention of a medicament.

On conventional spray-type preparations, it is recommendable to suck air from nose at the time of the spray operation, in order to prevent holding a medicament at nasal vestibule or prevent the sprayed preparation from dripping off from nasal cavity. However, it is thought that the elastic tissue of nasal valve narrows by sucking air, and then almost all of the preparation is carried from nose to mouth and finally swallowed.

The liquid-spraying device which has been usually used in the past is made for a spray-type preparation for liquid formulation wherein a liquid formulation is pumped up through a tube, which is generally used at an angle between about 0-25° (see FIG. 3). For this device, it is necessary to put the tip of the tube in the liquid, and thus the spray angle of the spray container for administration needs to be set at around 0° and a patient needs to tilt his/her head forward, which is a reason for setting at an angle between about 0-25°. However, using this administration system, a normal liquid formulation which has no viscosity or no adhesion, or is low viscosity will instantly run to nostril. On the contrary, using this administration system as a patient tilts his/her head back and the spray angle of the spray container for administration is set at about 65-90°, a normal spray-type liquid preparation sprayed will be hit on the intranasal wall such as turbinate and nasal septum, and then drained to inferior meatus of nose because of its non-adhesion, and mostly ended up being carried to his/her mouth and swallowed. It is partially possible to prevent the liquid from running to inferior meatus of nose by adding an adhesive polymer mentioned later as a substrate of the formulation. However, when an adhesive polymer is used therein, it is thought that the particle size of the formulation sprayed gets bigger; the liquid cannot be widely dispersed since the spray spreading-angle from the spray container gets smaller; the particles collide with each other in a nose to get bigger particles which is hit on the wall; and many of the formulation end up being carried to a mouth and swallowed. Further, it is expected that the liquid can be spread at a wide area of the turbinate by spraying it with wider spray angle, however, thereby it becomes impossible to put the tip of the tube for pumping up in the liquid in case of a conventional spray-type preparation. Therefore, there was some limitations to administer a liquid formulation as a patient tilts his/her head back and the spray angle of the spray container for administration is set at a desired angle.

In addition, the above-mentioned spray device for liquid is a system absorbing external air and thus it is necessary to use a certain amount of an antiseptic agent or other agent.

In addition, the particle size sprayed from the spray device to nasal cavity is also one of the factors to be considered in order to improve the clearance of a medicament. That is to say, the nasal cavity of a human has an area of about 150-180 cm$^2$, the distance from nostril to nasopharynx is 12-14 cm as a straight line which is very long, a nasal cavity has an optimized, narrow, and complicated geometric structure in order to protect the lower respiratory tract, and the narrow slit of the nasal valve causes about a half of the total air-resistance in nasal cavity. Further, there are some spaces partitioned in a slit like partition with turbinate in the backside of the nasal valve, where the speed of the formulation particles sprayed slows down and the particles can be contacted with nasal mucosa and dispersed. However, in such complicated and winding intranasal cavity, the formulation particles sprayed should been easily hit on the intranasal wall to be caught and deposited. Therefore, most of the formulation particles sprayed to nasal cavity whose particle size is 5 μm or more should be caught by the nasal cavity, then the formulation particles hit on the intranasal turbinate mucosa to be caught and deposited should be carried backward by means of the ciliary movement of ciliated cells covering the mucosa, and finally, via posterior nasal cavity and pharynx, drained to the month or swallowed. The countermeasure for the clearance of an active medicament which is taken as a foreign material by cilia and mucus (mucociliary clearance) is the most important factor on the design of a drug preparation for intranasal administration. The efficacy and the absorption of a medicament in nasal mucosa can be decided mainly based on the retention of a medicament (adhesive property of a formulation) and the permeability of a medicament at the capture part of nasal mucosa. A medicament administered to the effective capture part of nasal mucosa should disappear from the capture part as a simultaneous reaction mainly by means of the removal toward esophagus and respiratory tract due to the mucociliary clearance and the absorption to nasal mucosa cell via nasal mucosa. When the removal toward esophagus and respiratory tract from the effective capture part is quick, the clearance for the absorption to nasal mucosa cell should be reduced and the bioavailability thereof should be reduced. Or, the intranasal area which the formulation reaches can be improved to expand when the particle size of the sprayed formulation is micrified, however, thereby the risk that the formulation could reach lungs increases. Therefore, it has been understood for a skilled person to consider the balance of the particle size. Accordingly, in order to increase the clearance for the absorption to nasal mucosa and improve the absorption, it is important to optimize the particle size of the sprayed formulation, to spray in a suitable spray spreading-angle and an uniform spray spread, and further to add the retention of a medicament, i.e., adhesive property of a formulation for nasal mucosa, and thus it has been necessary to add an adhesive polymer as a base material for formulation to improve the property.

In theory, it is possible to spray a formulation for nose to take the formulation to the backside of the nasal valve by controlling the particle size of the sprayed formulation in a size of not more than 50 μm using a nebulizer, and inbreathing the sprayed particles at the time of spraying. However, using particles in a size of not more than 50 μm, a half or more of the particles should reach bronchi or lung, and thus a medicament to be held in intra cavity should disappear and additionally an undesirable side effect might happen. Further, the device for spray operation such as a nebulizer is expensive, and there was not any inexpensive and simple system to spread a formulation having an effective particle size in a whole intranasal cavity.

In order to improve the retention of a spray-type preparation in intranasal cavity, the present inventors have invented a gel base material for spray-administration to mucosa or skin, and have already disclosed a sprayable gel base material and a sprayable gel preparation comprising said base material and an active medicament, which can be applied to nasal cavity that is a mucosa site and is possible to use as a high-spreading spray-type preparation for nose (JP-B-2011069).

However, it has been already known as a serious problem that the viscosity should be reduced through spray operation even when a high viscous sprayable gel preparation is sprayed.

In addition, it is sometimes difficult to keep a constant amount of one spray shot when the spray angle for administration is rapidly changed, etc. because the sprayable gel-type preparation adheres on the sidewall of the spray container in being used as a spray-type preparation due to its high viscosity, the residual rate that indicates an unsprayed formulation retained in the container is high compared with a conventional liquid formulation, and the preparation cannot flow easily and rapidly in the spray container. Furthermore, it is also a problem that the formulation particles sprayed hardly reach the deep nasal cavity due to their particle size distribution, and it is difficult to adjust the spray spreading-angle and to spray in a uniform spray spread.

On a preparation for spray-administration to skin, there are also some similar problems to the above-mentioned preparation using a nasal spray such as the retention of the preparation, and the spray angle of the spray container for administration.

DISCLOSURE OF INVENTION

Problems to Be Solved by Invention

As mentioned above, with regard to a drug preparation for spray-administration to mucosa such as nasal cavity, eye, ear, oral cavity, rectum, vagina, and urethra, especially spray-type preparation for nose, it has been improved to some extent in case that sprayable gel base material is used as a liquid for formulation in order to improve the retention of the liquid. However, when a conventional spray device for nose is used, the above-mentioned problems such as high residual rate and inconstant spray amount may remain due to its retention and there is also a problem that the viscosity of a liquid for formulation is decreased by spray operation, and therefore it has been necessary to improve such problems. In addition, it is necessary to use a certain amount of an antiseptic agent or other agent because a conventional spray device for nose is a system absorbing external air, and thus some improvements have been necessary for safety and production cost.

Furthermore, from the viewpoint of the complicated structure of intranasal cavity, it is one of useful methods that the spray angle for administration is adjusted for the structure of intranasal cavity so that the sprayed formulation can be spread to a wide area of the turbinate, however, there is a certain limitation of the spray angle for administration of a liquid formulation using a conventional spray-type preparation for nose. Therefore, it has been desired to develop a new administration system capable of spraying at a suitable angle and spreading a sprayed formulation to a wide area of the turbinate and a new formulation for nasal spray capable of such system.

In addition, there have been also similar problems to the above-mentioned formulation for nasal spray on a drug preparation for spray-administration to skin such as hand, finger, leg, body, groin, scalp, the surround of anus, and the surround of genitalium.

Means to Solve the Problem

The present inventors have extensively studied on the above problem and have found an administration system comprising the sprayable gel-type skin/mucosa-adhesive preparation which is put in a spray container for a gel formulation (upper-pressure-relief airless-type spray container) that is different from a conventional spray container for nasal drop, which is characterized in that the administration direction of the spray container can be optionally set, i.e., the gel base material can be sprayed at any angle. Based upon the new findings, the present invention has been accomplished. In detail, it has got possible to prepare the above desired gel-type skin/mucosa-adhesive preparation by containing a certain constant amount of carboxy vinyl polymer and/or gellan gum in skin/mucosa-adhesive agent. Particularly, the inventors have found that the addition of gellan gum can prevent the viscosity of the preparation from lowering with nasal discharge, etc.

In addition, the inventors have found that it is possible to adjust the viscosity of the above formulation by adding an outside shearing force to the formulation to prepare a formulation having comparatively high viscosity (for example, 10000 mPa·s to 50000 mPa·s), which can make it possible to spray uniformly and completely prevent the viscosity of the formulation from lowering via the spray operation. Furthermore, surprisingly it has found that the viscosity of the formulation can be adjusted by adding a viscosity modulating agent and an outside shearing force so that the spray spreading-angle of the spray container and the spray spread can be set to meet the desired treatment. That is to say, the present inventors have found that the following tendency. With regard to a gel-type mucosa-adhesive preparation wherein the viscosity is adjusted with a shearing force, the spray spreading-angle sprayed from a spray container tends to be narrowed. On the contrary, in the case of adding a shearing force together with a viscosity modulating agent, the spray spreading-angle sprayed tends to be widen. Using this principle, it is possible to adjust the spray spreading-angle controlled to meet the purpose without using a variety of spray containers. In addition, the spray spread sprayed from a spray container tends to be localized at the periphery in using a gel-type mucosa-adhesive preparation adjusted with only a viscosity modulating agent without any shearing force. However, thanks to the finding that it is possible to spray in uniformity by adding a shearing force, it is possible to control the spray spread to meet the purpose by using these factors.

Furthermore, although such gel-type skin/mucosa-adhesive preparation is hard to be steadily sprayed because of its viscosity and adhesive property, and additionally it is hard to spray out the preparation in the container, it has been found that a spray container for a gel formulation (upper-pressure-relief airless-type spray container) can make it possible to spray in a constant amount and markedly improve the residual rate at the time of spraying out.

Especially, the present preparation for nasal spray using the formulation and the system can make it possible to spread the formulation to a wide area of the turbinate when spraying it to nasal cavity setting the body position for administration (the angle of patient's head) and the spray container at the effective angle.

Practically, the present invention provides a sprayable gel-type skin/mucosa-adhesive preparation comprising a gel formulation which contains an active pharmaceutical ingredient in a gel base material comprising a skin/mucosa-adhesive agent.

The present invention provides the above-mentioned sprayable gel-type skin/mucosa-adhesive preparation, wherein the applied mucosa is a mucosa of nasal cavity, eye, ear, oral cavity, rectum, vagina, or urethra; or the applied skin is a skin of hand, finger, leg, body, groin, scalp, the surround of anus, or the surround of genitalium. Especially, the present invention provides a gel-type mucosa-adhesive preparation for nasal spray comprising a gel formulation which contains an active pharmaceutical ingredient in a gel base material comprising a mucosa-adhesive agent.

In addition, the present invention provides the above-mentioned sprayable gel-type skin/mucosa-adhesive preparation, wherein the skin/mucosa-adhesive agent comprises carboxy vinyl polymer and/or gellan gum. Furthermore, the present invention provides the above-mentioned sprayable gel-type skin/mucosa-adhesive preparation, wherein the skin/mucosa-adhesive agent contains 0.1%(w/w) to 2.0%(w/w) carboxy vinyl polymer or gellan gum, or contains carboxy vinyl polymer and gellan gum in a total amount of 0.2% (w/w) to 4.0%(w/w).

In addition, the present invention provides the above-mentioned sprayable gel-type skin/mucosa-adhesive preparation, wherein the skin/mucosa-adhesive agent contains 0.1% (w/w) to 2.0% (w/w) carboxy vinyl polymer, and the viscosity thereof is adjusted by adding an outside shearing force. The adjusted viscosity is generally 50 mPa·s to 5000 mPa·s, preferably 100 mPa·s to 4000 mPa·s, more preferably 500 mPa·s to 3000 mPa·s, and the most preferably 2000 mPa·s to 2500 mPa·s.

Additionally, the present invention provides the above-mentioned gel-type skin/mucosa-adhesive preparation for nasal spray, which comprises 0.1% (w/w) to 2.0% (w/w) carboxy vinyl polymer as a skin/mucosa-adhesive agent, wherein by adding a viscosity modulating agent and an outside shearing force, the viscosity thereof is adjusted to make a comparatively high-viscous preparation (e.g. the viscosity of 10000 mPa·s to 50000 Mpa·s), and the spray spreading-angle from the spray container and the spray spread can be optionally set to meet the desired treatment. The inventor has found that the spray spreading-angle tends to become narrow by subjecting the gel formulation to the outside shearing force. The narrowed spray spreading-angle can be widened by adding a viscosity modulating agent, and thus the spray spreading-angle can be controlled through the two factors to meet the desired treatment. In addition, the outside shearing force can make the spray spread (which is localized at the periphery by adjusting only with a viscosity modulating agent) uniformalized. Therefore, from the viewpoint of this merit, the shearing force is useful to control the desired spray spread.

The viscosity modulating agent in the invention is preferably selected from a group consisting of sodium chloride, potassium chloride and calcium chloride. The controlled viscosity is generally 50 mPa·s to 5000 mPa·s, preferably 100 mPa·s to 4000 mPa·s, more preferably 500 mPa·s to 3000 mPa·s, and the most preferably 2000 mPa·s to 2500 mPa·s.

In addition, the present invention provides the above-mentioned sprayable gel-type skin/mucosa-adhesive preparation comprising a thickening agent for carboxy vinyl polymer which is selected from neutral or basic water-soluble amino acids and is contained in the weight range of 1:0.5 to 1:3 (preferably 1:1 to 1:2) against carboxy vinyl polymer. Furthermore, the thickening agent for carboxy vinyl polymer is preferably arginine, lysine, and/or ornithine.

And the present invention provides the above-mentioned sprayable gel-type skin/mucosa-adhesive preparation, wherein the gel formulation contains an active pharmaceutical ingredient in an amount of 0.001-10% (w/w) in the gel formulation.

Further, the present invention provides the above-mentioned sprayable gel-type skin/mucosa-adhesive preparation, wherein the active pharmaceutical ingredient is in a dissolved, suspended, or emulsified state.

The present invention provides an administration system comprising the above-mentioned sprayable gel-type skin/mucosa-adhesive preparation which is put in a spray container for a gel formulation (upper-pressure-relief airless-type spray container), which is characterized in that the administration direction of the spray container can be optionally set in order to spray the preparation to an affected part for the treatment, i.e., the gel base material can be sprayed at any angle. Especially, the present invention provides an administration system comprising the sprayable gel-type mucosa-adhesive preparation which is put in a spray container for a gel formulation (upper-pressure-relief airless-type spray container), wherein the preparation can be intranasally sprayed, optionally setting the spray spreading-angle from the spray container, in order to disperse and hold the gel preparation in a broad area of nasal cavity.

The present invention provides the above-mentioned administration system, wherein the viscosity of the gel formulation is in the range between 50 mPa·s and 5000 mPa·s (preferably 100 mPa·s and 4000 mPa·s), and the particle of the formulation sprayed via the spray operation has a viscosity retention rate of 50% or more.

The present invention provides the above-mentioned administration system, wherein the viscosity of the gel formulation is adjusted in the range between 50 mPa·s and 5000 mPa·s by adding an outside shearing force, and the particle of the formulation sprayed via the spray operation has a viscosity retention rate of 90% or more.

The present invention provides the above-mentioned administration system, wherein the mean particle size of the formulation sprayed is in the range between 10 μm and 100 μm (preferably between 50 μm and 100 μm).

The present invention provides the above-mentioned administration system, wherein by adding an outside shearing force (optionally adding viscosity modulating agent), the viscosity of the gel formulation is adjusted in the range between 50 mPa·s and 5000 mPa·s, the spray spreading-angle from the spray container is set in the range between 10° and 70°, and the spray spread is set in from uniformity through the periphery in order to meet the desired treatment.

The present invention provides the above-mentioned administration system, characterized in that the rate of the gel formulation staying in the spray container is not more than 20% (preferably not more than 15%, more preferably not more than 10%) when the spray operation has been completely impossible through the use, and the rate of the gel formulation sprayed in the range of the prefixed amount±10% is not less than 70% (preferably not less than 80%).

The present invention provides the above-mentioned administration system, wherein the spray angle of the spray container for administration can be set in any or all angle between 0° and 360°. In addition, the present invention provides the above-mentioned administration system for nasal spray, wherein the spray angle of the spray container for administration can be set in any or all angle between 45° and 180°.

The present invention provides the above-mentioned administration system, characterized in that the addition of an antiseptic agent or a preservative is omitted, or the said additive to be added to the formulation is decreased to 50% or less of the usual amount level.

The present invention also provides the above-mentioned administration system wherein a ring for reducing useless space is set in a spray container for a gel formulation (upperpressure-relief airless-type spray container), the body of slidable valve has a tilt angle of 5-30° (preferably 15-25°), and the ring also has the same tilt angle.

BEST MODE FOR CARRYING OUT THE INVENTION

Figure 1:
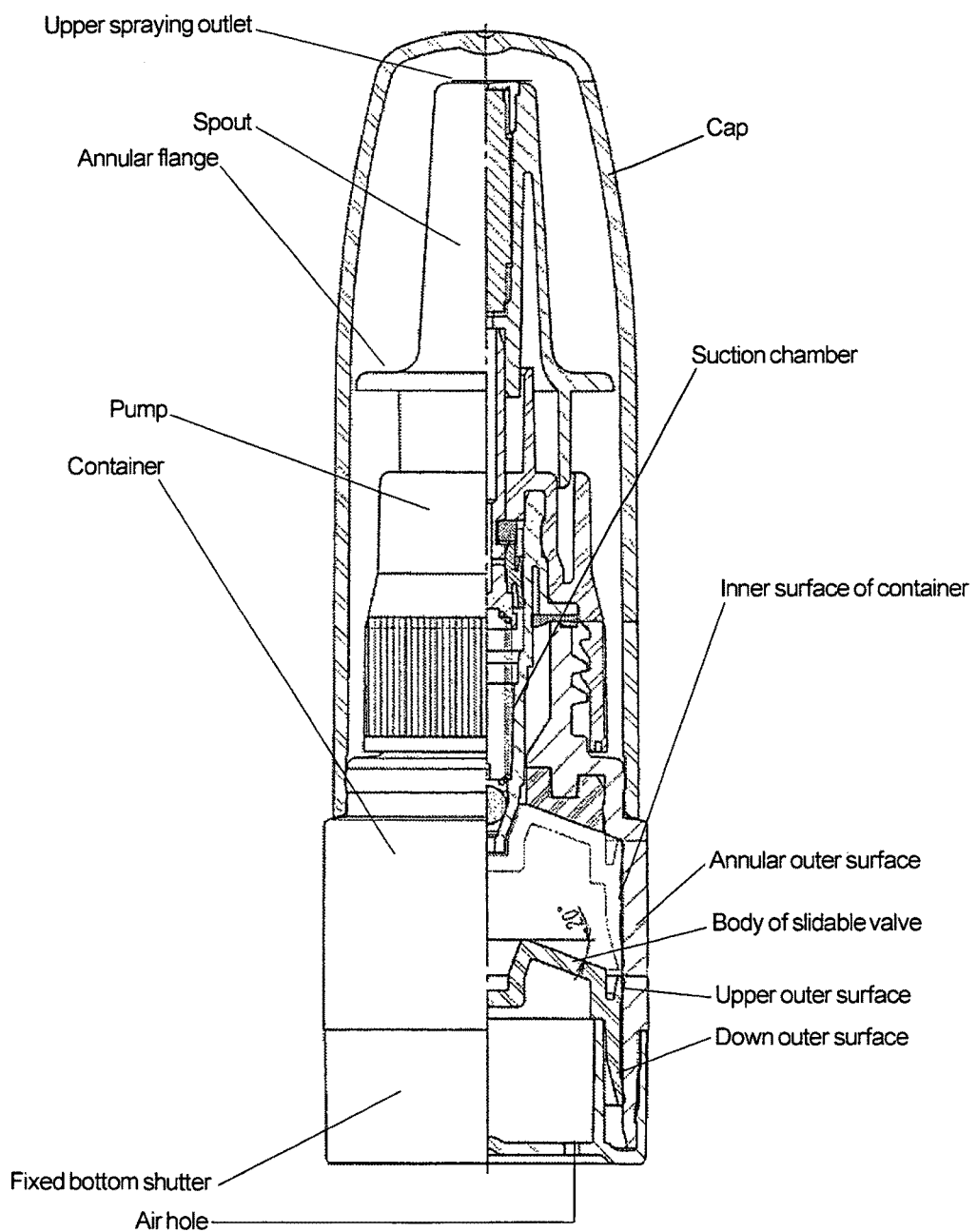
FIG. 1 shows a spray container for a gel formulation (upper-pressure-relief airless-type spray container) used herein. The right half plane of the drawing shows a cross-sectional view to see an internal structure.

The gel base material herein denotes a base material comprising a water-soluble polymer compound as a mucosa-adhesive agent, and water and/or alcohol(s), which has viscous property. The gel base material may include an antiseptic agent, a preservative, an isotonic agent, a pH regulator, a coloring agent, etc. which are conventionally used in pharmaceuticals.

The water-soluble polymer compound which is used as a skin/mucosa-adhesive agent (adhesive polymer) in the present invention, includes gum arabic, sodium alginate, propylene glycol alginate, carboxy vinyl polymer, carmellose sodium, xantham gum, gellan gum, gelatin, hydroxyethyl cellulose, hydroxypropyl cellulose, hydroxypropylmethyl cellulose, polyvinyl alcohol, methylcellulose, etc. It is possible to use a mucosa-adhesive agent prepared by combining 2 or more of the above-mentioned ingredients. Further, in order to (1) make the present formulation possess skin/mucosa-adhesiveness, (2) make the viscosity thereof retained or little changed through the spraying operation, (3) make the present formulation get to a target site (intranasal in the case of nasal use) with keeping the high viscosity, and (4) make the present formulation sprayed in a mean particle size of 10-100 μm (preferably 50-100 μm) which is enough fine, simultaneously; a gel base material comprising carboxy vinyl polymer or gellan gum, or a combination of carboxy vinyl polymer and gellan gum is preferably used as the adhesive polymer. As the base material comprising carboxy vinyl polymer, the gel base described in JP-B-2011069 "Spray gel base and spray gel preparation using thereof" whose inventor is the same as the present inventor may be used.

In addition, the gel base material may be controlled by (1) adjusting the viscosity of the formulation by adding an outside shearing force to carboxy vinyl polymer, or (2) adjusting the viscosity of the formulation by adding a viscosity modulating agent and an outside shearing force to carboxy vinyl polymer, so that the spray spreading-angle of the spray container and the spray spread can be set to meet the desired treatment.

The operation giving the shearing force herein can be carried out via a method known by a skilled person, wherein for example, a high-speed spinning-type emulsifying device, a colloidal mill-type emulsifying device, a high-pressure emulsifying device, a roll mill-type emulsifying device, an ultrasonic-type emulsifying device and a membrane-type emulsifying device can be used as a device giving shearing force. Especially, a homo mixer-type, a comb-type, and an intermittently-jet-stream-generating-type, high-speed spinning-type emulsifying devices are preferable.

The viscosity to be adjusted herein is ordinarily 50 mPa·s to 5000 mPa·s, preferably 100 mPa·s to 4000 mPa·s, more preferably 500 mPa·s to 3000 mPa·s, and most preferably 2000 mPa·s to 2500 mPa·s.

And, the spray spreading-angle used herein is defined as 0° when the gel formulation is sprayed in a straight line from the spray nozzle; and means an angle spreading from angle 0° that the gel formulation is sprayed. And, the spray spread means an index which indicates uniformity on the spread of the gel formulation sprayed. For example, it is denoted as "sprayed in uniformity", "localized at the periphery", etc. This evaluation of the spray spread was carried out by visually observing the gel formulation which was sprayed for a board from the spray nozzle and then adhered on the board.

The carboxy vinyl polymer which is used as an adhesive polymer in the present invention means a water-soluble polymer obtained by the polymerization with an acrylic acid used as a main ingredient, and includes a conventional polymer, for example, Carbopol® (Noveon, USA), etc. The concentration of carboxy vinyl polymer used in the present invention is generally about 0.1-2.0% (w/w). Gellan gum which is a polysaccharide produced by a microorganism, *Sphingomo-*

*nas elodea*, is generally used in a variety of food, etc. Especially, low acetyl gellan gum whose trade name is Gelrite®, and so on are preferably used. The concentration of gellan gum used in the present invention is generally about 0.1-2.0% (w/w). When carboxy vinyl polymer and gellan gum are used simultaneously and the formulation containing the two ingredients is sprayed and contacted with a nasal discharge (nasal mucus), the sensitivity of the nasal discharge (nasal mucus) against the ion of the formulation is reverse, thus the viscosity thereof gets lowered at first and the formulation once spreads in a wide area of a nasal cavity, and then the viscosity is retained (increased) to make it possible to long stay in a nasal cavity, which is an ideal profile. The total concentration of carboxy vinyl polymer and gellan gum used in the present invention is generally 0.2-4.0% (w/w), and the ratio of both is adjusted responding to the viscosity shift at a time when the formulation including an active medicament is contacted with nasal discharge (nasal mucus).

The thickening agent which is used for thickening carboxy vinyl polymer means a water-soluble basic material, which can neutralize and then ionize an acidic carboxy vinyl polymer, and thereby structurally magnify the carboxy vinyl polymer to thicken the carboxy vinyl polymer; and includes, for example, an inorganic base such as sodium hydroxide and potassium hydroxide; and an organic base such as an amine (e.g. diisopropanolamine, triethanolamine, and tripropanolamine), an amino acid (e.g. arginine, lysine, and ornithine); and preferably arginine, lysine, and ornithine. The thickening agent belonging to the amino acid above is generally contained in the weight range of 1:0.5 to 1:3, preferably 1:1 to 1:2 against carboxy vinyl polymer. The pH of the water-soluble basic material mentioned above may be adjusted to the desired range by neutralizing the carboxy vinyl polymer. The thickening agent may be used in combination with two or more of the above materials.

The "active pharmaceutical ingredient" dissolved in the gel base material herein means a pharmaceutical agent which is generally administered to the area of skin and/or mucosa, for example, a pharmaceutical agent for topically treating inflammation, allergy, etc., and a pharmaceutical agent which is expected to act on whole body through absorption from mucosa such as percutaneous absorption and nasal absorption are exemplified, but are not limited to them. The active pharmaceutical ingredient of the present invention which can be administered to the area of skin and/or mucosa includes, for example, a local vasoconstrictor such as naphazoline nitrate, tetrahydrozoline hydrochloride, oxymetazoline hydrochloride, and tramazoline hydrochloride; a steroid such as hydrocortisone, prednisolone, triamcinolone acetonide, dexamethasone phosphate, flunisolide, betamethasone phosphate, sodium beclomethasone dipropionate, fluticasone propionate, mometasone furoate, fluticasone furoate, budesonide, ciclesonide, betamethasone butyrate propionate, and diflucortolone valerate; a nonsteroidal antiinflammatory drug such as aspirin, mefenamic acid, ibuprofen piconol, suprofen, bufexamac, bendazac, ufenamate, diclofenac sodium, indomethacin, felbinac, ketoprofen, flurbiprofen, naproxen, pranoprofen, loxoprofen sodium, alminoprofen, zaltoprofen, piroxicam, meloxicam, lornoxicam, celecoxib, and rofecoxib; an antihistamine such as diphenhydramine, clemastine fumarate, triprolidine hydrochloride, isothipendyl hydrochloride, alimemazine tartrate, chlorpheniramine maleate, and promethazine hydrochloride; an anti-allergic agent such as cromolyn sodium, tranilast, ketotifen fumarate, amlexanox, azelastine hydrochloride, oxatomide, levocabastine hydrochloride, fexofenadine hydrochloride, epinastine hydrochloride, ebastine, cetirizine hydrochloride, bepotastine besilate, olopatadine hydrochloride, loratadine, ozagrel hydrochloride, seratrodast, pranlukast hydrate, zafirlukast, montelukast sodium, and suplatast tosilate; an antimicrobial agent such as nadifloxacin, clindamycin phosphate, levofloxacin, cefcapene pivoxil hydrochloride hydrate, clarithromycin, cefditoren pivoxil, vancomycin hydrochloride, meropenem hydrate, flomoxef sodium, cefotiam hexetil hydrochloride, and orbifloxacin; an antiherpesvirus drug such as acyclovir, valacyclovir hydrochloride, and vidarabine; an anti-cytomegalovirus agent such as ganciclovir, and foscarnet sodium hydrate; an anti-influenza virus agent such as oseltamivir phosphate, and zanamivir hydrate; an antifungal agent such as amphotericin B, fluconazole, itraconazole, micafungin sodium, terbinafine hydrochloride, neticonazole hydrochloride, lanoconazole, luliconazole, liranaftate, butenafine hydrochloride, and amorolfine hydrochloride; an antiseptic agent such as povidone-iodine, benzalkonium chloride, benzethonium chloride, and chlorhexidine gluconate; a local anesthetic such as lidocaine and dibucaine; an immunosuppressive agent such as cyclosporine and tacrolimus hydrate; an active vitamin $D_3$ drug such as tacalcitol, calcipotriol, alfacalcidol, calcitriol, and maxacalcitol; a drug for treating alopecia such as minoxidil and carpronium chloride; a drug for treating skin ulcer such as aluminum chlorohydroxy allantoinate, tretinoin tocoferil, bucladesine sodium, alprostadil alfadex, and trafermin; a vitamin $B_{12}$ drug such as cyanocobalamin and mecobalamin; a vitamin K drug such as phytonadione and menatetrenone; an antiplasmin such as epsilon-aminocaproic acid and tranexamic acid; an antiepileptic drug such as clonazepam, carbamazepine, and zonisamide; a hypnotic such as triazolam, brotizolam, zolpidem tartrate, quazepam, nitrazepam, and diazepam; an antidepressant such as paroxetine hydrochloride hydrate, etizolam, fluvoxamine maleate, milnacipran hydrochloride, and imipramine hydrochloride; an antipsychotic agent such as olanzapine, risperidone, and quetiapine fumarate; a drug for treating dementia such as donepezil hydrochloride and nicergoline; a drug for treating Parkinson's disease such as apomorphine, cabergoline, pergolide mesilate, bromocriptine mesilate, amantadine hydrochloride, and droxidopa; a drufg for treating cerebroprotective such as edaravone; an analgesic such as morphine, oxycodone, fentanyl, buprenorphine hydrochloride, and butorphanol tartrate; a stop smoking aid such as nicotine; a drug for treating migraine such as ergotamine tartrate, sumatriptan, zolmitriptan, eletriptan hydrobromide, rizatriptan benzoate, naratriptan, frovatriptan, almotriptan, and avitriptan; a vitamin such as cyanocobalamin, and mecobalamin; a sex steroid hormone such as estradiol, estriol, progesterone, and testosterone; a metal detoxification agent such as deferoxamine mesylate; an antitussive/antitussive drug such as codeine phosphate and isoproterenol hydrochloride; an antiemetic such as ondansetron hydrochloride, ramosetron hydrochloride, tropisetron hydrochloride, granisetron hydrochloride, metoclopramide, domperidone, and mosapride citrate; an anticancer agent such as goserelin acetate, bicalutamide, tegafur, paclitaxel, tamoxifen citrate, gemcitabine hydrochloride, doxifluridine, capecitabine, imatinib mesilate, rituximab, gefitinib, trastuzumab, paclitaxel, and docetaxel hydrate; an antihypertensive agent such as candesartan cilexetil, valsartan, losartan potassium, telmisartan, olmesartan medoxomil, amlodipine besylate, nifedipine, benidipine hydrochloride, nicardipine hydrochloride, nilvadipine, azelnidipine, manidipine hydrochloride, diltiazem hydrochloride, enalapril maleate, imidapril hydrochloride, temocapril hydrochloride, perindopril erbumine, carvedilol, bisoprolol fumarate, propranolol hydrochloride, and atenolol; a drug for treating dysuria such as tamsulosin hydrochloride and naftopidil; an antiulcer drug such as cimetidine, ranitidine hydrochloride, famotidine, and nizatidine; a cardiotonic agent such as dopamine hydrochloride and dobutamine hydrochloride; a bronchodilator such as fenoterol hydrobromide, ipratropium bromide, and oxitropium bromide; an anti-obesity agent such as mazindol and peptide YY; an autonomic agent such as neostigmine methylsulfate; a drug for treating angina such as nitroglycerin, isosorbide dinitrate, and nicorandil; an antiplatelet agent such as ticlopidine hydrochloride, cilostazol, sarpogrelate hydrochloride, and beraprost sodium; an antidiabetic drug such as voglibose, acarbose, glimepiride, nateglinide, metformin hydrochloride, pioglitazone hydrochloride, and gliclazide; a lipid-lowering drug such as pravastatin sodium, simvastatin, fluvastatin sodium, atorvastatin calcium hydrate, pitavastatin calcium, rosuvastatin calcium, and bezafibrate; an antiarrhythmic drug such as pilsicainide hydrochloride, mexiletine hydrochloride, and disopyramide phosphate; a muscle relaxant such as baclofen, piracetam, eperisone hydrochloride, and tizanidine hydrochloride; an antirheumatic drug such as bucillamine, methotrexate, infliximab, prednisolone farnesylate, and actarit, additionally an LHRH (luteinizing hormone-releasing hormone) as a peptide/proteinaceous drug; a growth hormone-releasing factor; a somatostatin derivaative; a posterior pituitary hormone such as vasopressin and desmopressin acetate; an oxytocin; a hirudin derivative; an enkephalin; a ACTH (adrenocorticotropic hormone) derivative; a bradykinin derivative; an insulin; a glucagon derivative; a growth hormone; a growth hormone-releasing hormone; a luteinizing hormone; an insulin-like growth factor; a calcitonin gene-related peptide; an atrial natriuretic peptide derivative; an interferon; an interleukin; an erythropoietin; a granulocyte colony-stimulating factor; a macrophage colony-stimulating factor; a parathyroid hormone; parathyroid hormone-releasing hormone; a prolactin; a thyrotropin-releasing hormone; an angiotensin; a calcitonin; a Gn-RH (Gonadotropin releasing hormone) derivative such as leuprorelin acetate, buserelin acetate, and nafarelin acetate; a thrombolytic drug such as tisokinase, alteplase, monteplase, pamiteplase, and nasaruplase; a vaccine such as influenza HA vaccine, pneumococcal vaccine, and recombinant adsorbed hepatitis B vaccine. The active pharmaceutical ingredient may be contained in 0.001-10% (w/w), but the content thereof is not limited. And the gel formulation may contain plural active pharmaceutical ingredients.

When an active medicament insoluble in water is used, a formulation containing the medicament may become clouded. However, the active medicament is not precipitated and hence it is no problem to use it via a normal spray operation. On the contrary, it is preferable to use a solubilizer in the formulation or to prepare the formulation with the active medicament that is dissolved in a water-soluble organic solvent in advance, when an active medicament soluble in a formulation can be more absorbed in a target site (nasal mucosa in case of nasal spray). The water-soluble organic solvent includes a lower alcohol such as ethanol and isopropanol; a glycol such as propylene glycol, 1,3-butylene glycol, and polyethylene glycol having a molecular weight of 300-500. In addition, the solubilizer used herein can be selected from a variety of surfactants, depending on the solubility of the active medicament.

In addition, it is useful to suspend an active medicament by adding an appropriate suspending-agent. The suspending agent includes, for example, a variety of surfactants such as a sucrose fatty acid ester, polyoxyl 40 stearate, polyoxyethylene (60) hydrogenated castor oil polyoxyethylene, polysorbate 80, glyceryl monostearate, sorbitan monostearate, and sorbitan monopalmitate.

Further, it is also useful to emulsify the gel base material by adding an appropriate emulsifying agent and then to add an active medicament thereto; or to emulsify the active medicament itself. The emulsifying agent used herein can be selected from a variety of surfactants.

The term "mucosa" used herein refers to an epithelial layer originated from ectoderm, covered in epithelial cell; and as an example thereof, nasal cavity, eye, ear, oral cavity, rectum, vagina, genitalium, urethra, anus, etc. are exemplified. And, the term "skin" used herein refers to a layer covering body surface; and the example thereof includes a layer of hand, finger, leg, body, groin, scalp, the surround of anus, the surround of genitalium, etc.

The term "skin/mucosa" used herein means "skin and/or mucosa," which is used in order to cover a target site that has both skin and mucosa, such as the surround of anus, or the surround of genitalium.

The viscosity defined herein can be measured, for example, by the viscosity measurement by capillary tube viscometer, the viscosity measurement by rotational viscometer, etc., which are described in Viscosity Determination in the Japanese Pharmacopoeia (General Tests section).

The viscosity of the gel formulation used herein is generally 50 mPa·s to 5000 mPa·s, preferably 100 mPa·s to 4000 mPa·s, more preferably 500 mPa·s to 3000 mPa·s, and most preferably 2000 mPa·s to 2500 mPa·s.

The term "viscosity retention rate" defined herein refers to a rate of the viscosity of the formulation particle that has just been sprayed against that of the pre-sprayed gel formulation.

In the present invention, the viscosity retention rate of the formulation particle sprayed via the present spray operation is preferably 50% or more.

The mean particle size of the formulation particle sprayed in the present invention can be measured for example with a particle size analyzer which uses a laser light scattering method.

The mean particle size thereof in the present invention is preferably in the range of 10 μm to 100 μm, and further preferably in the range of 50 μm to 100 μm.

The "residual rate" defined herein refers to a rate of the amount of the gel formulation which stays in the spray container for a gel formulation (upper-pressure-relief airless-type spray container) at the time when the gel-type mucosa-adhesive preparation for nasal drop is sprayed out and the spray operation cannot be carried out, per the total amount before using.

The residual rate of the present invention is generally 20% or less, preferably 15% or less, and more preferably 10% or less.

The "prefixed amount" defined herein refers to an amount or amount-range of the formulation that is sprayed through one-shot of the nasal spray, which is fixed beforehand. For example, when it is defined that about 100 mg of the formulation is sprayed through one-shot of the spray operation, the prefixed amount is 100 mg.

In the present invention, it is preferable that the formulation sprayed in the prefixed amount±10% is 70 % or more, and more preferably 80% or more.

The antiseptic agent defined herein includes, but are not limited to, benzalkonium chloride and benzethonium chloride. The preservative includes, but is not limited to, a paraben such as methylparaben and propylparaben. Herein, the usual amount of an additive means an additive amount which is permitted, for example, as the pharmaceutical approval, which is easily guessed with the amount of an approved pharmaceutical, a structure thereof, etc. by a skilled person.

The spray container for a gel formulation (upper-pressure-relief airless-type spray container) used herein includes a container as exemplified in FIG. 1 of the attached drawings.

The spray container is an airless pump container which is operated as follows:
removing the cap of the container; and
depressing the annular flange of the pump which is attached on the head of the container
to spray from the spraying outlet the content in the suction chamber of the pump which was already sucked from the container inside, and simultaneously
to slide the body of slidable valve up, relating with the absorption as vacating the container inside, wherein the circumference of the body of slidable valve is prepared so that the annular outer surface of the body can move like a seal closely contacting the inner surface of the container.

Figure 2:
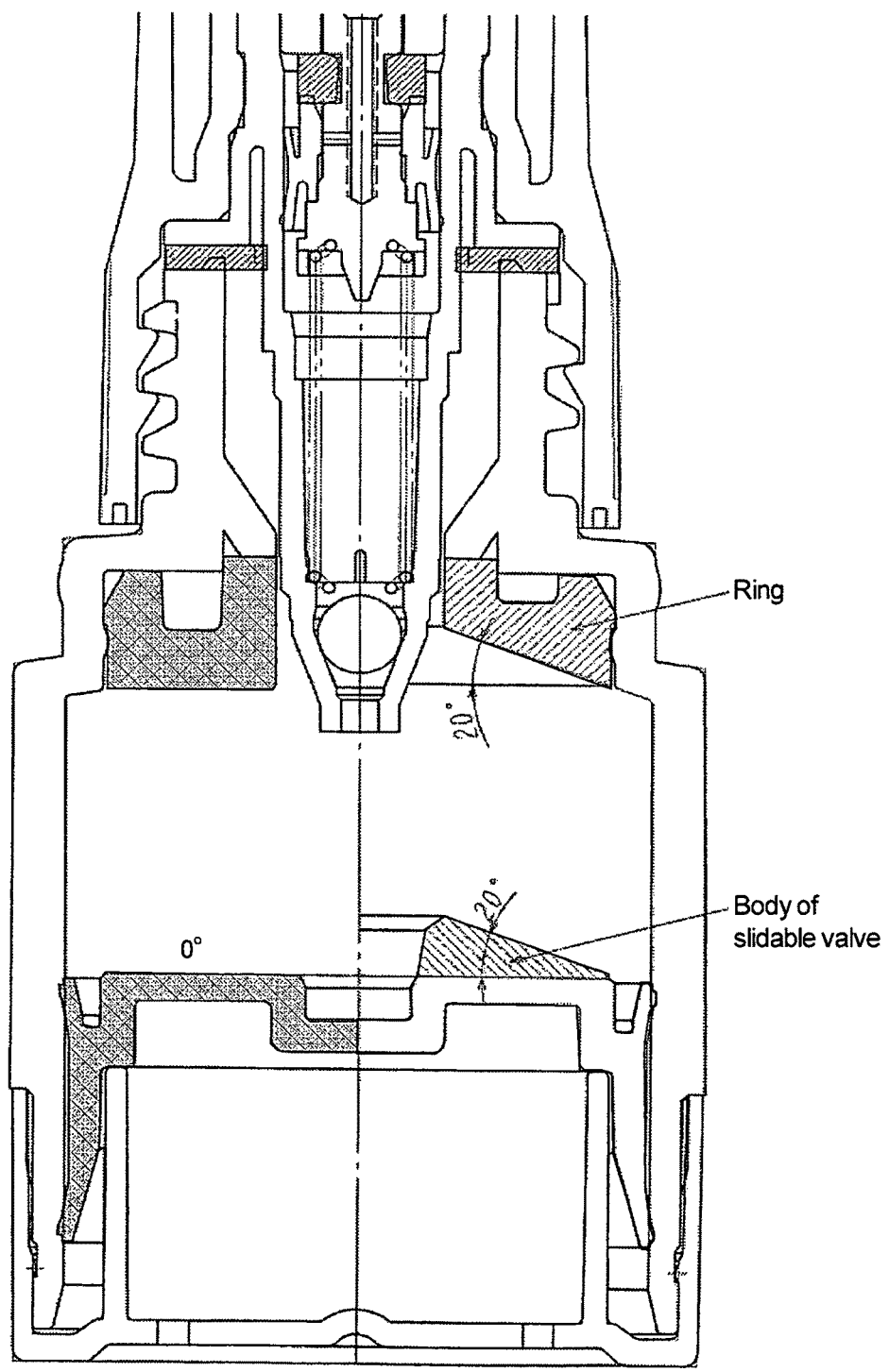
FIG. 2 shows a magnified figure of the main part in the cross-sectional view shown in FIG. 1 of the spray container for a gel formulation (upper-pressure-relief airless-type spray container). The right half plane shows a container wherein the body of slidable valve has a certain tilt angle (as an example, 20° in the drawing) which is a feature of the present invention, while the left half plane shows a conventional upper-pressure-relief airless-type spray container.

A spray container having the above-mentioned mechanism has been already published as an airless pump container provided that it does not mention the use for nasal spray (JP-A-2003-212262). However, it has been desired to reduce useless space which does not contribute to the spray operation to a maximum extent, and to make it possible to smoothly replace air in the suction chamber with a formulation when charging the suction chamber, as a (upper-pressure-relief airless-type) spray container for the gel-type formulation like the present invention. Especially, it was anticipated that the residual amount in the container at the time that the non-fluid gel-type formulation of the present invention was sprayed out would be more than that of a conventional formulation because of its bad retention. Thus, the inventors have further improved the conventional airless spray container, i.e., setting a ring for reducing useless space as shown in the right half plane of FIG. 2, and further having a certain tilt angle on the body of slidable valve which is ordinarily an even face. Through the improvements, the inventors have found that it is possible to easily remove air in the container and further to almost completely remove the dead volume by setting a ring having the same tilt angle to almost completely fit the faces between the body of slidable valve and the ring at the time of spraying out. Thus, the present inventors have found a system which the residual amount can be very little at the time of spraying out. Furthermore, the spray container for a gel formulation (upper-pressure-relief airless-type spray container) which is used in the present invention and has the above properties as shown in FIGS. 1 and 2 can provide a precise spraying amount as an ordinary pharmaceutical. When the certain tilt angle of the body of slidable valve is small, there can retain an airspace in the shoulder part of the body of the container; while when the angle is big, there can retain an airspace in the lower part of the slidable valve; both are inconvenient. The angle is preferably 5-30°, more preferably 15-25°.

In addition, the spray container for a gel formulation (upper-pressure-relief airless-type spray container) used herein is not a system absorbing external air, and thus has a very useful property as a pharmaceutical preparation that it is hard to suffer microorganism-contamination from external air. Therefore, the spray container is a very useful administration system for nasal spray from the viewpoint of safety and production cost because it is not required to use any excessive antiseptic agent or preservative.

Figure 3:
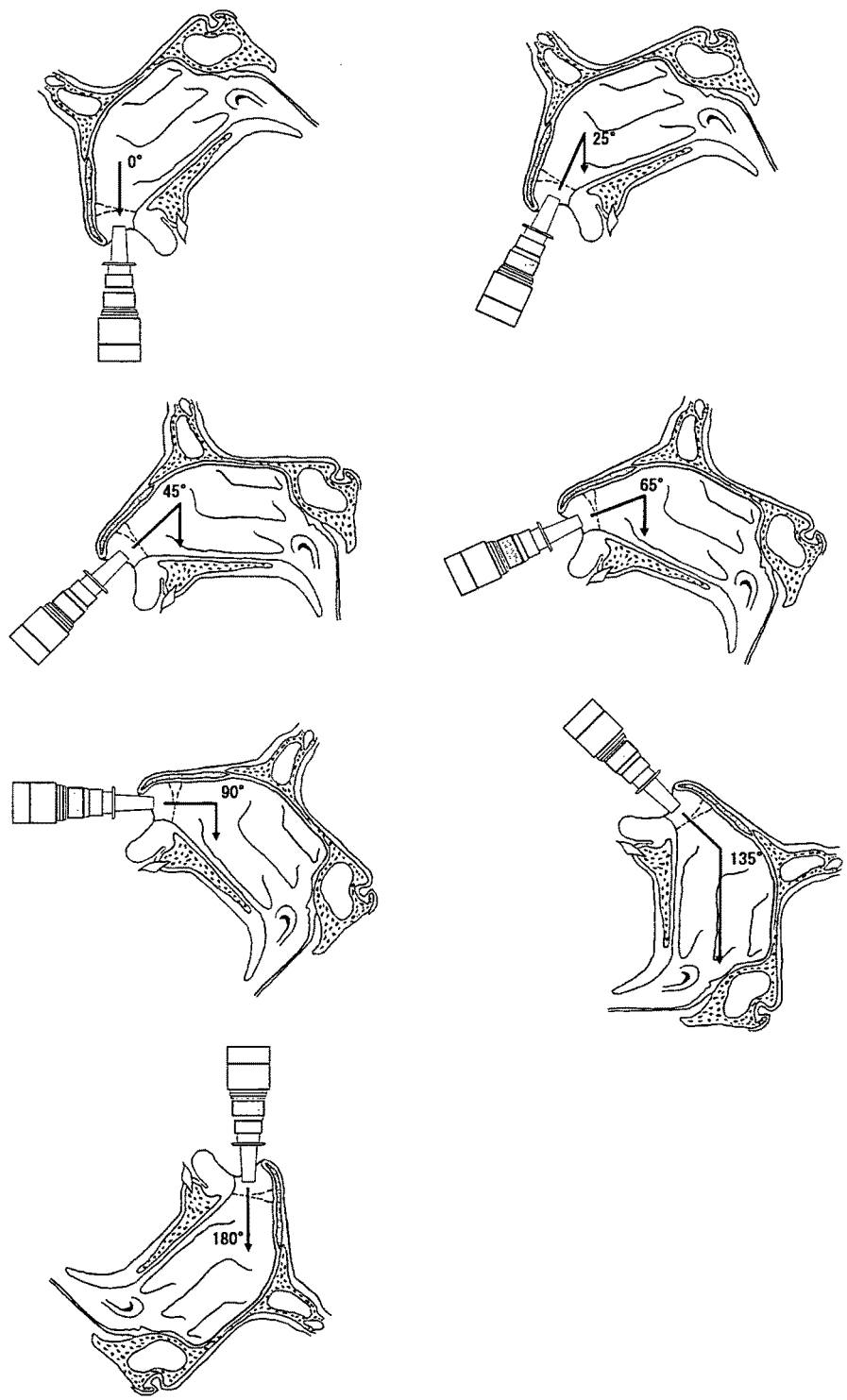
FIG. 3 shows some states that the present preparation for nasal spray is inserted in human turbinate (nasal meatus) in various angles and administered. It is defined as an angle of 0° that the spray preparation is set vertically. The figures show 7 examples administered in 25°, 45°, 65°, 90°, 135° and 180°.

The spray angle of the spray container for administration in the invention can be used setting in any or all angle between 0° and 360°. For example, the above-mentioned sprayable preparation for nasal spray can be used so that the body position for administration (the angle of patient's head) and spray angle of the spray container for administration can be varied as shown in FIG. 3 of the attached drawings. That is to say, the present preparation can be sprayed in any angles: i.e., around 0° which is an available angle in a conventional nasal spray, 45°-90° which is hard to be sprayed, and 180° which is impossible to be sprayed.

In the present invention, when tilting patient's head backward and using the spray container in an angle of 65-180°, the turbinate (nasal meatus) is thought to be changed from parallel direction to vertical direction so that the formulation can be dispersed and adhered on the tip of the turbinate at first. And then, the formulation captured/adhered in the turbinate will be carried backward by means of gravity and ciliary movement of ciliated cells covering a mucosa to spread in a wide area of the turbinate.

Therefore, the angle between the body position for administration and the spray angle of spray container for administration may be set in any angle of 0°-180°, preferably 45°-180°, further preferably 65°-180°, most preferably around 1350 in which the turbinate (nasal meatus) is set in a vertical direction, and it is the most advantageous to spread in a wide area of the turbinate. The body position may be selected from standing position, sitting position, lying position on one's back, lying position on one's side, etc., i.e. any position is available. The preparation for nasal spray of the invention can be used in any spray angle for administration.

EXAMPLE

Hereinafter, the invention is illustrated based on examples and experiments, but are not limited thereto. Some preparations of the present invention which were formulated with an actual active pharmaceutical ingredient were shown in the latter part hereof as preparation examples, while for some physicochemical tests, the following 9 kinds of gel-type skin/mucosa-adhesive preparations which had each different viscosity were prepared with some ingredients mentioned below, without any active pharmaceutical ingredient, and subjected to the following physicochemical tests.

In the following examples and experiments, each viscosity was measured at 20° C. with a viscometer type C.

Examples 1-3 are gel formulations which are prepared by adding the same amount of sodium chloride as a viscosity modulating agent to each formulation without using any shearing force, which have viscosities of 1000, 2000 and 3000 mPa·s, respectively. (The viscosities of Example 1-3 which are prepared without adding sodium chloride as a viscosity modulating agent are 31000 mPa·s, 35000 mPa·s, and 36000 mPa·s, respectively.)

Examples 4-7 are gel formulations which are prepared with a shearing force. To Examples 6 and 7 is further added sodium chloride as a viscosity modulating agent together with a shearing force. Each viscosity of Examples 4-7 is adjusted to 2500 mPa·s. (The viscosity of Example 4 which is prepared without using any shearing force is 23000 mPa·s. The viscosity of Example 5 which is prepared without using any shearing force and the viscosities of Example 6 and Example 7 which are prepared without using sodium chloride as a viscosity modulating agent and any shearing force are all 34000 mPa·s.)

Example 8 is a formulation having the same composition as Example 4-7, wherein the viscosity is adjusted to 2500 mPa·s with a viscosity modulating agent, without any shearing force. (The viscosity of Example 8 which is prepared without adding sodium chloride as a viscosity modulating agent is 34000 mPa·s.)

A comparative example as a control formulation of Examples 4-8 was prepared without using any viscosity modulating agent or any outside shearing force, wherein the viscosity was 2500 mPa·s.

| | Quantity (%(w/w)) | | |
|---|---|---|---|
| Ingredients | Example 1 | Example 2 | Example 3 |
| carboxy vinyl polymer | 0.42 | 0.53 | 0.56 |
| L-arginine | 0.74 | 0.95 | 1.0 |
| disodium edetate | 0.05 | 0.05 | 0.05 |
| polysorbate 80 | 0.1 | 0.1 | 0.1 |
| concentrated glycerin | 1.0 | 1.0 | 1.0 |
| sodium chloride | 0.5 | 0.5 | 0.5 |
| purified water | 97.19 | 96.87 | 96.79 |
| Total | 100% | 100% | 100% |
| Detected viscosity | 1000 mPa·s | 2000 mPa·s | 3600 mPa·s |

| | Quantity (%(w/w)) | | | | | |
|---|---|---|---|---|---|---|
| Ingredients | Example 4 | Example 5 | Example 6 | Example 7 | Example 8 | Comparative Example |
| carboxy vinyl polymer | 0.25 | 0.5 | 0.5 | 0.5 | 0.5 | 0.085 |
| L-arginine | 0.5 | 1.0 | 1.0 | 1.0 | 1.0 | 0.17 |
| sodium chloride | — | — | 0.125 | 0.25 | 0.5 | — |
| purified water | 99.25 | 98.5 | 98.375 | 98.25 | 98.0 | 99.745 |
| Total | 100% | 100% | 100% | 100% | 100% | 100% |
| Detected viscosity | Adjustment of viscosity: adjusting the viscosity to 2500 mPa·s by using shearing force, i.e., by rotating the formulation at 15,000 rpm under cooling in an intermittently-jet-stream-generating-type high-speed spinning-type emulsifying device (Type: CLM-0.8S). | | | | 2500 mPa·s | 2500 mPa·s |

The containers used for the tests are the following spray container which can spray about 100 mg in one operation.

Container of the present invention: a spray container for a gel formulation (upper-pressure-relief airless-type spray container) (100 mg-sprayable pump, charged amount: 5 g).

Control container (1): a spray container of a commercial preparation which has a double structure, wherein the inside structure is in a mortal-form, characterized by minimizing the remaining amount in the container (100 mg-pump, charged amount: 5 g).

Control container (2): a conventional spray container (100 mg-pump, charged amount: 5 g).

Tests for Remaining Amount in the Container, Amount Sprayed within the Prefixed Range, and Spray Frequency About 5.0 g of each formulation of Example 1-Example 8 was exactly weighed and put into the three kinds of spray containers: container of the invention, control container (1) and control container (2) which were weighed in the vacant state beforehand. The containers were tilted at the angle between 0°-180° shown in Tables 1 and 2. The spray amount of every one-shot of the spray operation was measured by calculating the weight difference between before and after shot, and the measurement was repeated until the formulation was sprayed out almost completely. Table 1 shows the result using the container of the invention, and Table 2 shows using the control containers.

In addition, as a distribution (%) of the formulation put in the container after spraying out, the remains (%) in the container at the time that the spray operation with the pump gets impossible, "formulation (%) sprayed within 100±10 mg" which denotes the rate of the cumulative amount of the formulation sprayed in the range of the prefixed amount (100 mg)±10%, per the total amount of the formulation, and "formulation (%) sprayed outside 100±10 mg" which denotes the rate of the formulation sprayed outside the range were calculated using the following formulas. The results are also shown in Tables 1 and 2.

Remains in the container (%)=Remains in the container (g)/Initial fill amount (g)×100

Formulation (%) sprayed within 100±10 mg=The cumulative amount (g) of the formulation sprayed in the range of 100±10 mg/Initial fill amount (g)×100

Formulation (%) sprayed outside 100±10 mg=The cumulative amount (g) of the formulation sprayed outside the range of 100±10 mg/Initial fill amount (g)×100

Furthermore, the frequency of the shots which could be sprayed in the range of 100±10 mg is shown therein.

TABLE 1

Test results using the container of the invention

| Container type | Spray angle for administration | Formulation | Viscosity (mPa·s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 0° | Example 1 | 1000 | 7.1 | 87.8 | 5.1 | 44 |
| | | Example 2 | 2000 | 7.2 | 87.6 | 5.2 | 44 |
| | | Example 3 | 3600 | 7.3 | 87.7 | 5.0 | 44 |
| | | Example 4 | 2500 | 7.1 | 87.9 | 5.0 | 44 |
| | | Example 5 | 2500 | 7.2 | 87.7 | 5.1 | 44 |
| | | Example 6 | 2500 | 7.2 | 87.8 | 5.0 | 45 |
| | | Example 7 | 2500 | 7.2 | 87.6 | 5.2 | 44 |
| | | Example 8 | 2500 | 7.1 | 87.9 | 5.0 | 45 |
| | 25° | Example 2 | 2000 | — | — | — | — |
| | | Example 7 | 2500 | 7.1 | 87.8 | 5.1 | 45 |
| | 45° | Example 2 | 2000 | 7.1 | 87.7 | 5.2 | 44 |
| | | Example 7 | 2500 | 7.2 | 87.6 | 5.2 | 44 |
| | 65° | Example 2 | 2000 | 7.1 | 87.4 | 5.5 | 44 |
| | | Example 7 | 2500 | 7.1 | 87.7 | 5.2 | 45 |
| | 90° | Example 2 | 2000 | 7.1 | 87.8 | 5.1 | 44 |
| | | Example 7 | 2500 | 7.2 | 87.5 | 5.3 | 44 |
| | 180° | Example 2 | 2000 | 7.1 | 87.7 | 5.2 | 44 |
| | | Example 7 | 2500 | 7.2 | 87.8 | 5.0 | 45 |

TABLE 2

Test results using control container (1) and control container (2)

| Container type | Spray angle for administration | Formulation | Viscosity (mPa·s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Control container (1) | 0° | Example 1 | 1000 | 24.4 | 65.4 | 10.2 | 33 |
| | | Example 2 | 2000 | 27.7 | 61.0 | 11.3 | 31 |
| | | Example 3 | 3600 | 31.3 | 54.7 | 14.0 | 28 |
| | | Example 4 | 2500 | 26.2 | 62.1 | 11.7 | 32 |
| | | Example 5 | 2500 | 28.1 | 59.7 | 12.2 | 30 |
| | | Example 6 | 2500 | 27.3 | 60.0 | 12.7 | 30 |
| | | Example 7 | 2500 | 28.4 | 58.4 | 13.2 | 30 |
| | | Example 8 | 2500 | 28.0 | 59.7 | 12.3 | 30 |
| Control container (2) | 0° | Example 1 | 1000 | 28.5 | 55.1 | 16.4 | 28 |
| | | Example 2 | 2000 | 32.8 | 47.2 | 20.0 | 24 |
| | | Example 3 | 3600 | 38.6 | 39.2 | 22.2 | 20 |
| | | Example 4 | 2500 | 30.9 | 50.5 | 18.6 | 26 |
| | | Example 5 | 2500 | 31.6 | 49.2 | 19.2 | 25 |
| | | Example 6 | 2500 | 31.8 | 48.1 | 20.1 | 24 |
| | | Example 7 | 2500 | 32.7 | 47.3 | 20.1 | 24 |
| | | Example 8 | 2500 | 34.5 | 46.8 | 18.7 | 24 |

When using the present system using the container of the present invention, the distribution rate (%) of the formulation put in the container after spraying out could be almost constant even if the formulation is highly viscous, i.e. it is almost constant without being affected by the viscosity or the spray angle for administration. The results showed that the remains amount in the container were low (about 7.1%), and the formulation amount sprayed within the prefixed range was high (about 87.7%). While, when using Control container (1) and Control container (2), the distribution rate was affected by the viscosity as shown in the following Table 2, i.e., the remains amount in the containers increased and the formulation amount sprayed within the prefixed range decreased as the viscosity rose.

Hereinafter, the results shown in the above Table 1 and Table 2 were re-constituted by classifying the results on the basis of the spray angle for administration and the kind of the preparations, and the re-constituted results are shown in Table 3-Table 8.

Figure 4:
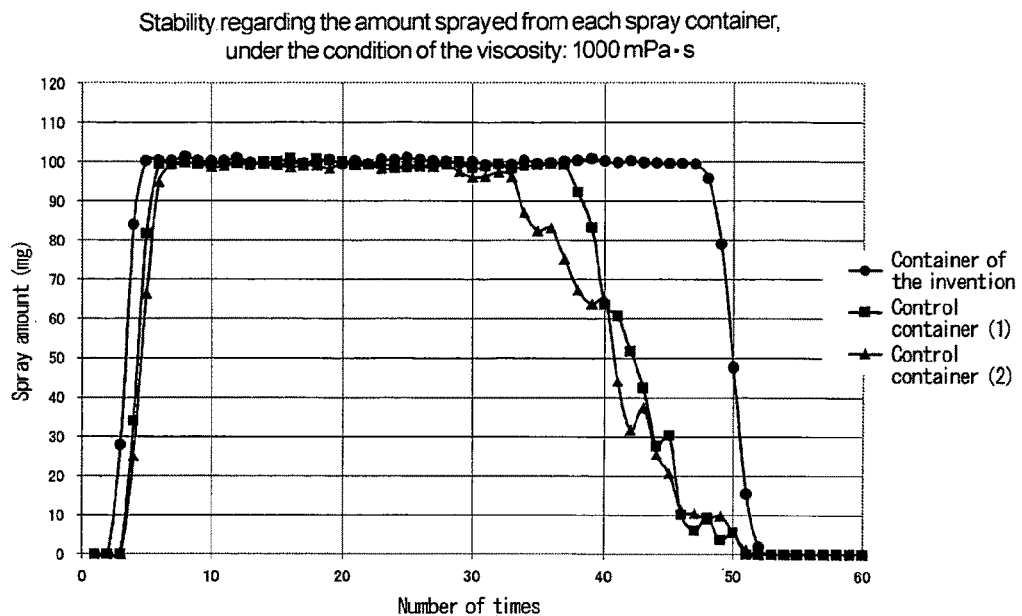
FIG. 4 shows the stability regarding the amount sprayed from each spray container, under the condition of the viscosity: 1000 mPa·s (spray angle for administration: 0°).
Figure 5:
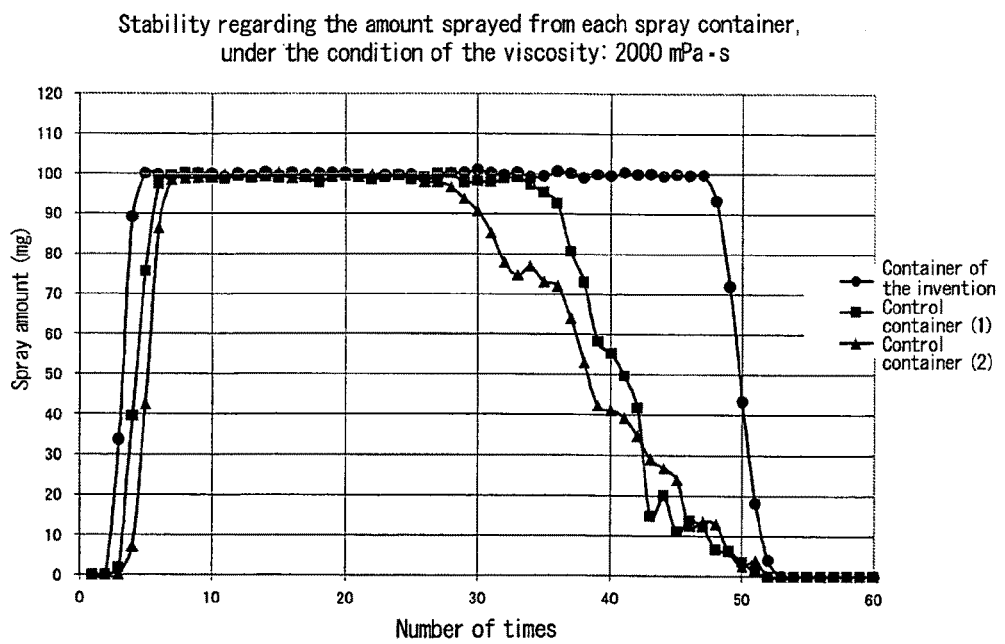
FIG. 5 shows the stability regarding the amount sprayed from each spray container, under the condition of the viscosity: 2000 mPa·s (spray angle for administration: 0°).
Figure 6:
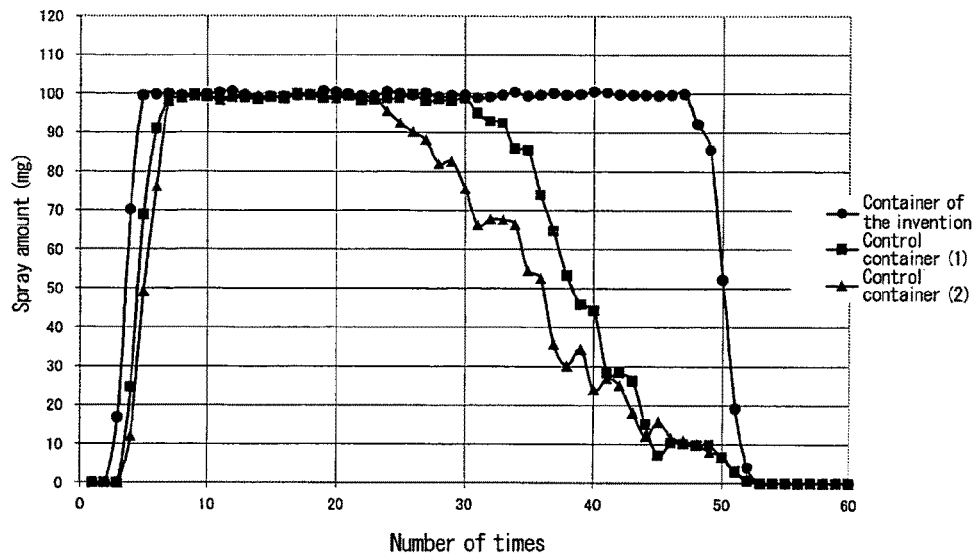
FIG. 6 shows the stability regarding the amount sprayed from each spray container, under the condition of the viscosity: 3600 mPa·s (spray angle for administration: 0°).

The results wherein the spray angle for administration is 0° are summarized in Table 3, Table 4 and Table 5 which are classified on the basis of each viscosity and each spray container. The results have shown that the present system using the container of the invention is very useful. In addition, FIG. 4, FIG. 5 and FIG. 6 graphed on the basis of the results in Table 3-Table 5 show the relation between the viscosity and the stability regarding the sprayed amount comparing between each spray container. These graphs also show that the present system is useful.

TABLE 3

Distribution rate (%) of the formulation after spraying out which has viscosity (1000 mPa · s) in each spray container

| Container type | Spray angle for administration | Formulation | Viscosity (mPa · s) | Distribution (%) of the formulation put in the container after spraying out ||| Count of shots sprayed within 100 ± 10 mg |
| --- | --- | --- | --- | --- | --- | --- | --- |
| | | | | Remains in the container | Formulation sprayed within 100 ± 10 mg | Formulation sprayed outside 100 ± 10 mg | |
| Container of the invention | 0° | Example 1 | 1000 | 7.1 | 87.8 | 5.1 | 44 |
| Control container (1) | | Example 1 | 1000 | 24.4 | 65.4 | 10.2 | 33 |
| Control container (2) | | Example 1 | 1000 | 28.5 | 55.1 | 16.4 | 28 |

TABLE 4

Distribution rate (%) of the formulation after spraying out which has viscosity (2000 mPa · s) in each spray container

| Container type | Spray angle for administration | Formulation | Viscosity (mPa · s) | Distribution (%) of the formulation put in the container after spraying out ||| Count of shots sprayed within 100 ± 10 mg |
| --- | --- | --- | --- | --- | --- | --- | --- |
| | | | | Remains in the container | Formulation sprayed within 100 ± 10 mg | Formulation sprayed outside 100 ± 10 mg | |
| Container of the invention | 0° | Example 2 | 2000 | 7.2 | 87.6 | 5.2 | 44 |
| Control container (1) | | Example 2 | 2000 | 27.7 | 61.0 | 11.3 | 31 |
| Control container (2) | | Example 2 | 2000 | 32.8 | 47.2 | 20.0 | 24 |

TABLE 5

Distribution rate (%) of the formulation after spraying out which has viscosity (3600 mPa · s) in each spray container

| Container type | Spray angle for administration | Formulation | Viscosity (mPa · s) | Distribution (%) of the formulation put in the container after spraying out ||| Count of shots sprayed within 100 ± 10 mg |
| --- | --- | --- | --- | --- | --- | --- | --- |
| | | | | Remains in the container | Formulation sprayed within 100 ± 10 mg | Formulation sprayed outside 100 ± 10 mg | |
| Container of the invention | 0° | Example 3 | 3600 | 7.3 | 87.7 | 5.0 | 44 |
| Control container (1) | | Example 3 | 3600 | 31.3 | 54.7 | 14.0 | 28 |
| Control container (2) | | Example 3 | 3600 | 38.6 | 39.2 | 22.2 | 20 |

Figure 7:
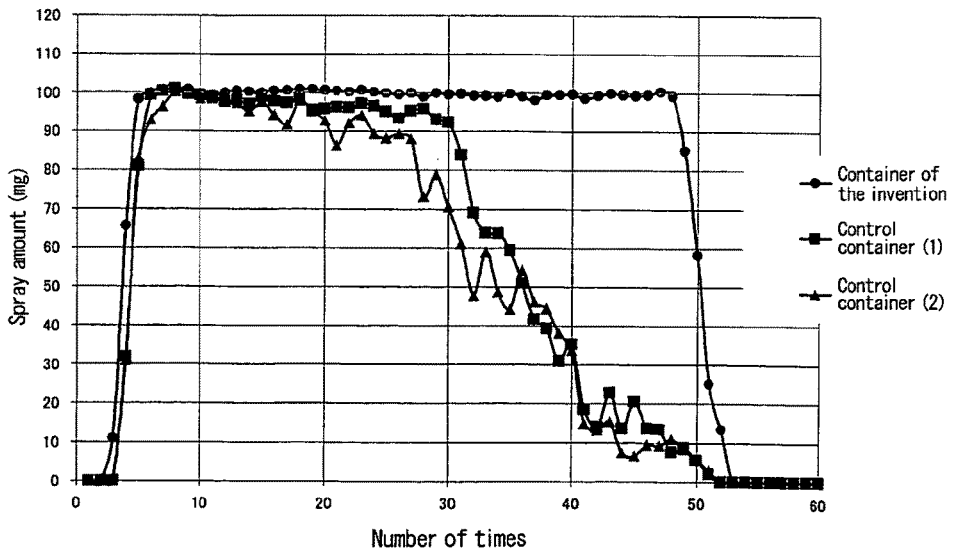
FIG. 7 shows the stability regarding the amount sprayed from each spray container, under the condition of the spray angle for administration: 450 (viscosity: 2000 mPa·s).
Figure 8:
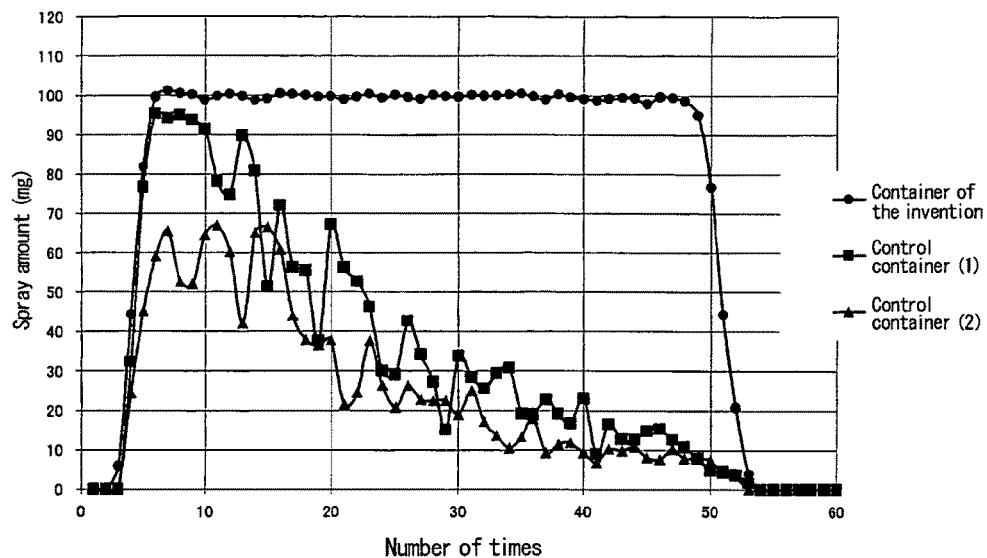
FIG. 8 shows the stability regarding the amount sprayed from each spray container, under the condition of the spray angle for administration: 65° (viscosity: 2000 mPa·s).
Figure 9:
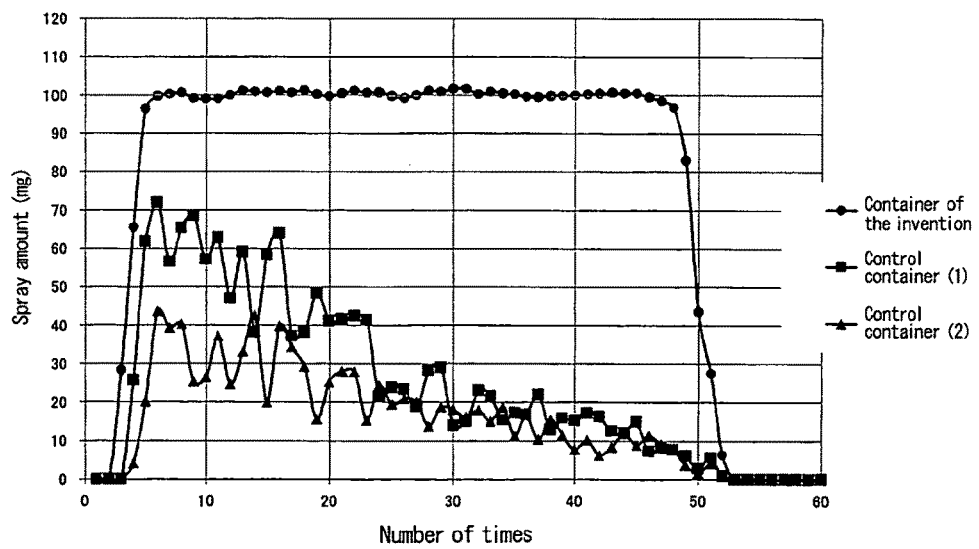
FIG. 9 shows the stability regarding the amount sprayed from each spray container, under the condition of the spray angle for administration: 90° (viscosity: 2000 mPa·s).

In addition, the results of the distribution (i) of the formulation put in the container after spraying out, wherein Example 2 or Example 7 is selected as a content of the preparation, are summarized in Table 6-Table 11 which are classified on the basis of each spray angle for administration and each spray container. The results have shown that the present system using the container of the invention has a low residual rate and enable a very stable spray in any spray angle. In addition, FIG. 7-FIG. 9 graphed on the basis of the results in Table 6-Table 8 show the relation between the spray angle for administration and the stability regarding the sprayed amount comparing between each spray container. These graphs show that it is only the system of the present invention to be able to use in a spray angle of 65° or 90°.

TABLE 6

Distribution rate (%) of the formulation after spraying out which has viscosity (2000 mPa · s) and spray angle (45°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 45° | Example 2 | 2000 | 7.1 | 87.7 | 5.2 | 44 |
| Control container (1) | | Example 2 | 2000 | 35.7 | 48.5 | 15.8 | 25 |
| Control container (2) | | Example 2 | 2000 | 40.3 | 34.3 | 25.4 | 18 |

TABLE 7

Distribution rate (%) of the formulation after spraying out which has viscosity (2000 mPa · s) and spray angle (65°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 65° | Example 2 | 2000 | 7.1 | 87.4 | 5.5 | 44 |
| Control container (1) | | Example 2 | 2000 | 60.7 | 9.4 | 29.9 | 5 |
| Control container (2) | | Example 2 | 2000 | 72.8 | 0.0 | 27.2 | 0 |

TABLE 8

Distribution rate (%) of the formulation after spraying out which has viscosity (2000 mPa · s) and spray angle (90°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 90° | Example 2 | 2000 | 7.1 | 87.8 | 5.1 | 44 |

TABLE 8-continued

Distribution rate (%) of the formulation after spraying out which has viscosity (2000 mPa · s) and spray angle (90°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Control container (1) | | Example 2 | 2000 | 70.7 | 0.0 | 29.3 | 0 |
| Control container (2) | | Example 2 | 2000 | 81.4 | 0.0 | 18.6 | 0 |

TABLE 9

Distribution rate (%) of the formulation after spraying out which has viscosity (2500 mPa · s) and spray angle (45°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 45° | Example 7 | 2500 | 7.1 | 87.9 | 5.0 | 45 |
| Control container (1) | | Example 7 | 2500 | 36.1 | 46.8 | 17.1 | 24 |
| Control container (2) | | Example 7 | 2500 | 47.2 | 30.5 | 22.3 | 15 |

TABLE 10

Distribution rate (%) of the formulation after spraying out which has viscosity (2500 mPa · s) and spray angle (65°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 65° | Example 7 | 2500 | 7.2 | 87.5 | 5.3 | 44 |
| Control container (1) | | Example 7 | 2500 | 62.9 | 8.1 | 29.0 | 4 |
| Control container (2) | | Example 7 | 2500 | 79.2 | 0.0 | 20.8 | 0 |

TABLE 11

Distribution rate (%) of the formulation after spraying out which has viscosity (2500 mPa · s) and spray angle (90°) in each spray container

| Container type | Spray angle for administration | Formulation | Viscosity (mPa · s) | Remains in the container | Formulation sprayed within 100 ± 10 mg | Formulation sprayed outside 100 ± 10 mg | Count of shots sprayed within 100 ± 10 mg |
|---|---|---|---|---|---|---|---|
| Container of the invention | 90° | Example 7 | 2500 | 7.1 | 87.8 | 5.1 | 45 |
| Control container (1) | | Example 7 | 2500 | 77.5 | 0.0 | 22.5 | 0 |
| Control container (2) | | Example 7 | 2500 | 84.5 | 0.0 | 15.5 | 0 |

Comparison of Mean Particle Size

Each mean particle size of the gel-type skin/mucosa-adhesive preparations of the present invention and other gel-type skin/mucosa-adhesive preparations which were sprayed was measured with a particle size analyzer which uses a laser light scattering method and analyzed (Table 12). The containers used herein were all the same spray container for a gel formulation (upper-pressure-relief airless-type spray container).

It has been found that the sprayed gel-type skin/mucosa-adhesive preparation of the present invention has a small particle size, especially an ideal particle size (50-100 μm) as a drug preparation for intranasal administration, though it is highly viscous.

TABLE 12

Comparison of mean particle size of each formulation

| Formulation | Viscosity (mPa · s) | Spray angle of spray container for administration | Mean particle size (μm) |
|---|---|---|---|
| Example 1 | 1000 | 0° | 74.8 |
| Example 2 | 2000 | 0° | 75.3 |
| Example 3 | 3600 | 0° | 87.5 |
| Example 4 | 2500 | 0° | 71.1 |
| Example 5 | 2500 | 0° | 233.4 |
| Example 6 | 2500 | 0° | 69.8 |
| Example 7 | 2500 | 0° | 66.6 |
| Example 8 | 2500 | 0° | 77.3 |
| Comparative example | 2500 | 0° | 77.5 |
| hydroxypropyl cellulose | 1000 | 0° | 294.1 |
| hydroxypropyl cellulose | 2000 | 0° | 531.6 |
| carmellose sodium | 400 | 0° | 88.4 |
| carmellose sodium | 1000 | 0° | 192.5 |
| carmellose sodium | 2000 | 0° | 254.9 |

Comparison of Viscosity Retained Through Spraying Operation

Each viscosity of the gel-type skin/mucosa-adhesive preparation of the present invention and other gel-type skin/mucosa-adhesive preparation at the time before/after spraying was measured and the variation due to spraying was compared each other (Table 13). The containers used herein were all the same spray container for a gel formulation (upper-pressure-relief airless-type spray container). It has been found that it is only the gel-type skin/mucosa-adhesive-preparation of the present invention to exhibit a very high viscosity retention rate. Especially, in Examples 4-7 which were prepared by adding a shearing force to adjust the viscosity, there was no variation of the viscosity at the time before/after spraying, and it was a very high viscosity retention rate.

TABLE 13

Comparison of viscosity retained through spraying operation

| Formulation | Viscosity before spraying (mPa · s) | Viscosity after spraying (mPa · s) | Viscosity retention rate (%) |
|---|---|---|---|
| Example 1 | 1000 | 850 | 85.0 |
| Example 2 | 2000 | 1750 | 87.5 |
| Example 3 | 3600 | 3200 | 88.9 |
| Example 4 | 2500 | 2500 | 100.0 |
| Example 5 | 2500 | 2500 | 100.0 |
| Example 6 | 2500 | 2500 | 100.0 |
| Example 7 | 2500 | 2500 | 100.0 |
| Example 8 | 2500 | 2180 | 87.2 |
| Comparative example | 2500 | 1010 | 40.4 |
| hydroxypropyl cellulose | 1000 | 55 | 5.5 |
| hydroxypropyl cellulose | 2000 | 120 | 6.0 |
| carmellose sodium | 400 | 1 | 0.3 |
| carmellose sodium | 1000 | 18 | 1.8 |
| carmellose sodium | 2000 | 75 | 3.8 |

Comparison of Spray Spreading-angle and Spray Spread Through Spraying Operation

Using each of the above-prepared gel-type skin/mucosa-adhesive preparations which have different viscosities and are prepared via different processes, spray spreading-angle and spray spread thereof were measured, and compared each other (Table 14). The containers used herein were all the same spray container for a gel formulation (upper-pressure-relief airless-type spray container).

Each spray spreading-angle was not affected by the difference of each viscosity (see, for example, the comparison between Examples 1-3). In Examples 4-7 which were gel-type mucosa-adhesive preparations prepared by adding a shearing force to adjust the viscosity, each spray spreading-angle tended to be narrowed. Amongst these examples, Example 6 and Example 7 comprising sodium chloride as a viscosity modulating agent tended to exhibit a wider spray spreading-angle compared with Example 5 which did not comprise sodium chloride.

In addition, each spray spread was also affected by the addition of a shearing force. That is to say, it has been found that in Examples 1-3 and Example 8 to which a shearing force was not added, each spray spread was localized at the periphery, while, in Examples 4-7 to which a shearing force was added, each spray spread was uniform (see FIGS. 10-13).

From these findings, the gel-type skin/mucosa-adhesive preparation of the present invention can be controlled by adjusting the viscosity by adding a viscosity modulating agent and an outside shearing force, so that the spray spreading-angle from a spray container, and the spray spread can meet a purpose. For example, when the active pharmaceutical ingredient is an ionic compound and is in a solution state, it is possible to adjust the spray spreading-angle from a spray container and uniformalize the spray spread by adding only an outside shearing force, because the ingredient works as a viscosity modulating agent.

TABLE 14

Comparison of spray spreading-angle and spray spread through spraying operation

Figure 10:
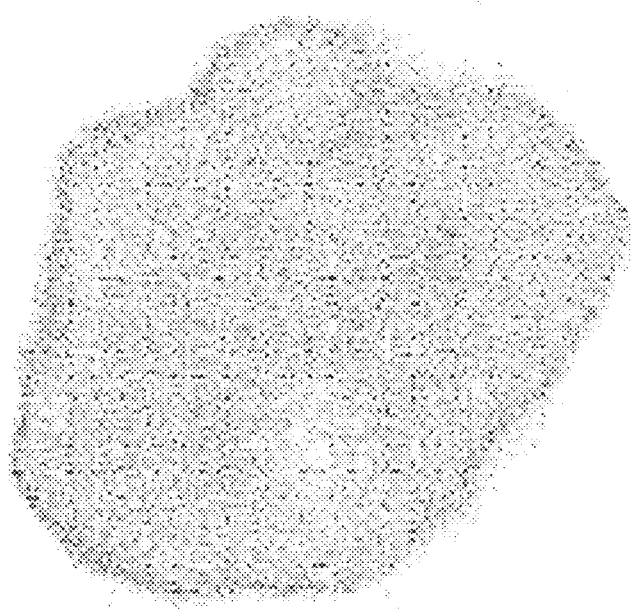
FIG. 10 shows the figure of the spray spread that is observed in Example 5 wherein the viscosity is adjusted to 2500 mPa·s by -adding 0 % sodium chloride and an outside shearing force.
Figure 11:
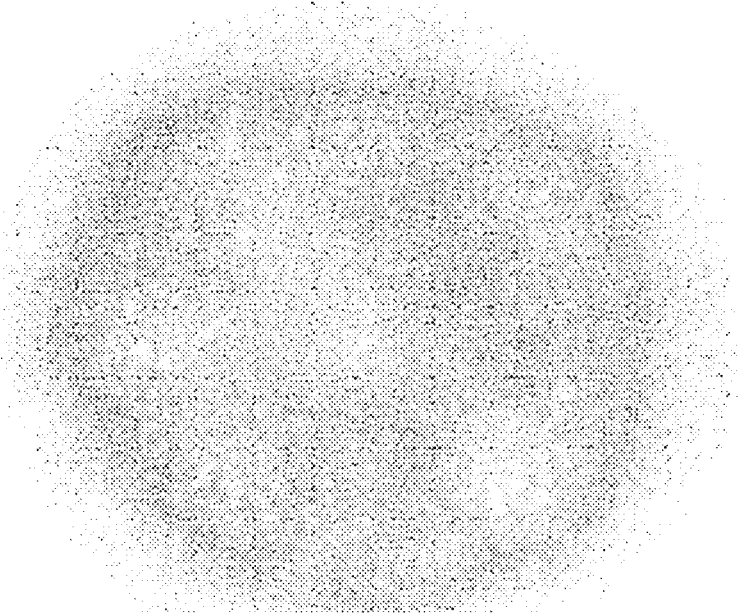
FIG. 11 shows the figure of the spray spread that is observed in Example 6 wherein the viscosity is adjusted to 2500 mPa·s by adding 0.125% sodium chloride and an outside shearing force.
Figure 12:
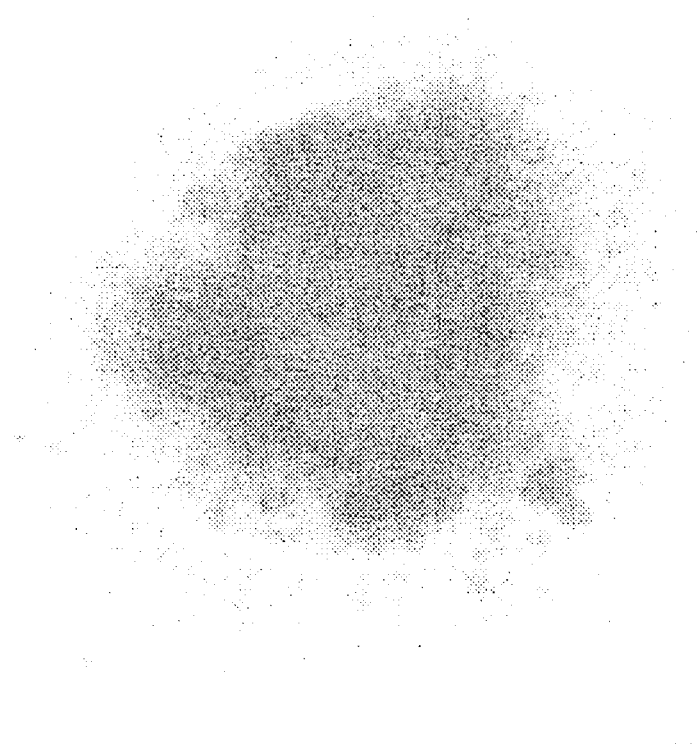
FIG. 12 shows the figure of the spray spread that is observed in Example 7 wherein the viscosity is adjusted to 2500 mPa·s by adding 0.25% sodium chloride and an outside shearing force.
Figure 13:
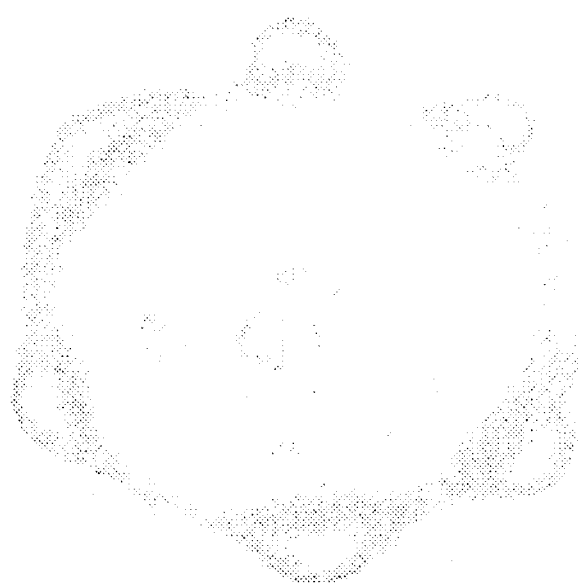
FIG. 13 shows the figure of the spray spread that is observed in Example 8 wherein the viscosity is adjusted to 2500 mPa·s by adding 0.50 % sodium chloride, without outside shearing force.

| Formulation | Spray spreading-angle | Spray spread Result | Reference figure |
|---|---|---|---|
| Example 1 | 57.8 | localized at the periphery | — |
| Example 2 | 57.3 | localized at the periphery | — |
| Example 3 | 56.0 | localized at the periphery | — |
| Example 4 | 46.4 | sprayed in uniformity | — |
| Example 5 | 18.8 | sprayed in uniformity | FIG. 10 |
| Example 6 | 40.5 | sprayed in uniformity | FIG. 11 |
| Example 7 | 45.5 | sprayed in uniformity | FIG. 12 |
| Example 8 | 57.5 | localized at the periphery | FIG. 13 |

Comparison of Viscosity of the Formulation Varied with Prepared Nasal Discharge

Using the following ingredients, gel-type skin/mucosa-adhesive preparations comprising gellan gum were prepared. The above preparations, Example 4-Example 8, and Comparative example were subjected to a comparison-experiment about the viscosity variation using a prepared nasal discharge (the composition is shown below).

The prepared nasal discharge is a liquid preparation comprising similar ions and similar concentration thereof to human nasal discharge. The prepared nasal discharge was added to each preparations, and the mixtures were made to be uniformalized. After about 5 minutes, each viscosity was measured. (The amount of the prepared nasal discharge added was shown as an amount added to 10 g of each preparation).

| Ingredients | Quantity (%(w/w)) Example 9 | Example 10 |
|---|---|---|
| carboxy vinyl polymer | 0.15 | 0.35 |
| gellan gum | 0.15 | 0.15 |
| L-arginine | 0.30 | 0.70 |
| sodium chloride | — | 0.27 |
| purified water | 99.40 | 98.53 |
| Total | 100% | 100% |
| Detected viscosity | 2500 mPa · s | 2500 mPa · s |

[Composition of Prepared Nasal Discharge]

| | |
|---|---|
| NaCl | 6.81 g |
| KCl | 1.91 g |
| $CaCl_2 \cdot 2H_2O$ | 0.59 g |
| $MgCl_2 \cdot 6H_2O$ | 0.13 g |
| Total | 1000 mL |

The above "prepared nasal discharge" is prepared based on the composition described in the *Japanese Society of Public Health* (*Morio SABURI*, et al., Vol. 39, No. 6, P 341-P 346, 1992).

Figure 14:
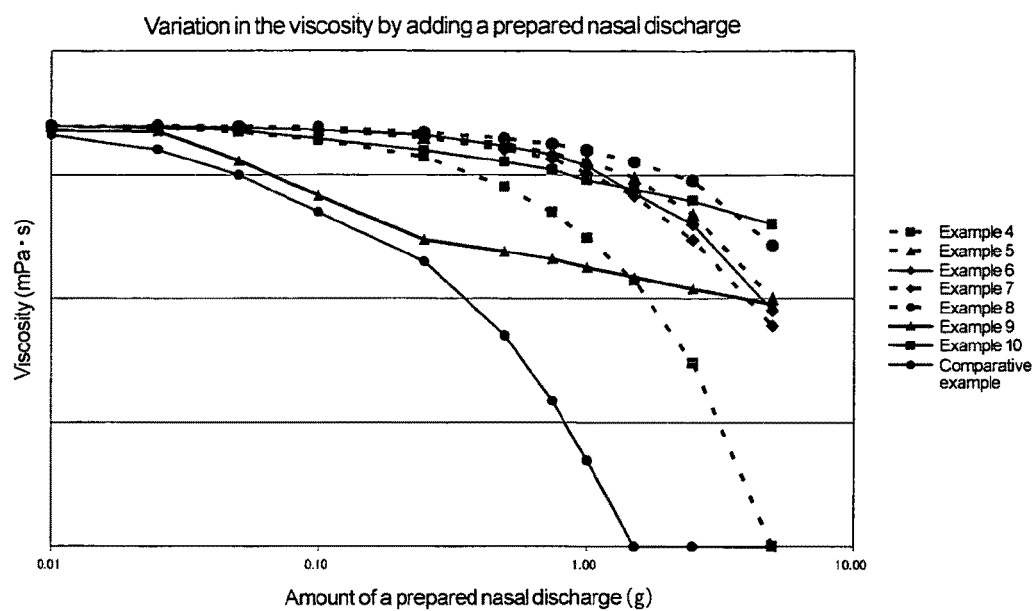
FIG. 14 shows the variation in the viscosity of Example 4-Example 10 and the comparative example by adding a prepared nasal discharge.

The variation in the viscosity of each gel-type mucosa-adhesive preparation of the present invention by adding a prepared nasal discharge is shown in FIG. 14. All the containers used in the experiment were the same spray container for a gel formulation (upper-pressure-relief airless-type spray container). In Comparative example wherein the viscosity was not adjusted by adding a viscosity modulating agent or an outside shearing force, it was observed that the viscosity was markedly decreased by adding the prepared nasal discharge. While, in Examples 4-10 wherein the viscosity was adjusted with either of the above-mentioned treatments, the lowering of the viscosity could be stopped to a high degree. Especially, it should be noted that Examples 9 and 10 which contain gellan gum were more resistant to be affected at the viscosity change by increasing the added prepared nasal discharge than the other Examples which do not contain gellan gum.

Comparison of Stability Against Microorganism 0.2% Gellan gum solution was heat-sterilized to be a content of the preparation. The spray container for a gel formulation (upper-pressure-relief airless-type spray container) and Control container (2) which were EOG-sterilized were charged with 5 g of the content. 2.5 g of the content was sprayed from each container until the remaining amount of the content in each container should be 50%, and each container was stored in an incubator at 37° C., or at room temperature. Each amount of microorganism was observed over time, and the stability of each container against microorganism was compared each other (Table 15). It was indicated that the stability against microorganism using the spray container for a gel formulation of the present invention is superior to that of the conventional container for nasal spray.

TABLE 15

Comparison of stability against microorganism

| Formulation | Container | In incubator at 37° C. | At room temperature |
|---|---|---|---|
| 0.2% gellan gum solution | Container of the invention | No change over time. | No change over time. |
| 0.2% gellan gum solution | Control container (2) | Microorganism colony was visibly observed after 3 weeks. | Microorganism colony was visibly observed after 7 weeks. |

Comparison of Intranasal Retention Using Saccharin Preparation

The preparation prepared by adding saccharin sodium (having sweet taste) to the formulation of Example 2 wherein the concentration of saccharin sodium is 0.5%, and 0.5% saccharin sodium solution in water were nasally administered (each one shot to both nostrils, total: 200 mg) to subjects (3 subjects: A, B, C) in a variety of angles using nasal spray container for a gel formulation (upper-pressure-relief airless-type spray container) equipped with a pump which can be sprayed in 100 mg per a shot. A certain period after administration, the head of each subject was set in a vertical direction. The time that was needed from the administration until the time when a subject begins to taste sweet in each trial was recorded and compared each other (Table 16-Table 19). In all cases, the gel-type skin/mucosa-adhesive preparation of Example 2 needed even more time than the normal non-gel type solution for each subject to begin to taste sweet, thus it was indicated that the intranasal retention of the gel-type preparation was sufficiently high.

TABLE 16

Comparison of intranasal retention using saccharin preparation
(The case that the head was set in a vertical direction shortly after the administration.)

| Spray angle | | Preparation comprising 0.5% saccharin Na of Example 2 | | | 0.5% saccharin Na solution in water | |
|---|---|---|---|---|---|---|
| 0° | A | 32 min 10 sec | Average | A | 3 min 15 sec | Average |
| | B | 37 min 30 sec | 37 min 12 sec | B | 4 min 30 sec | 4 min 22 sec |
| | C | 41 min 55 sec | | C | 5 min 20 sec | |
| 25° | A | 29 min 45 sec | Average | A | 5 min 10 sec | Average |
| | B | 39 min 45 sec | 35 min 57 sec | B | 3 min 35 sec | 3 min 37 sec |
| | C | 38 min 20 sec | | C | 2 min 05 sec | |
| 45° | A | 28 min 20 sec | Average | A | 4 min 15 sec | Average |
| | B | 36 min 35 sec | 34 min 40 sec | B | 2 min 30 sec | 3 min 22 sec |
| | C | 39 min 05 sec | | C | 3 min 20 sec | |
| 65° | A | 31 min 15 sec | Average | A | 2 min 20 sec | Average |
| | B | 35 min 05 sec | 35 min 58 sec | B | 1 min 45 sec | 1 min 48 sec |
| | C | 41 min 35 sec | | C | 1 min 20 sec | |
| 90° | A | 33 min 25 sec | Average | A | 45 sec | Average |
| | B | 39 min 25 sec | 39 min 35 sec | B | 15 sec | 23 sec |
| | C | 45 min 55 sec | | C | 10 sec | |

TABLE 17

Comparison of intranasal retention using saccharin preparation
(The case that the head was set in a vertical direction 15 sec. after the administration.)

| Spray angle | | Preparation comprising 0.5% saccharin Na of Example 2 | | | 0.5% saccharin Na solution in water | |
|---|---|---|---|---|---|---|
| 65° | A | 36 min 05 sec | Average | A | 55 sec | Average |
| | B | 39 min 05 sec | 39 min 50 sec | B | 1 min 15 sec | 1 min 02 sec |
| | C | 44 min 20 sec | | C | 55 sec | |
| 90° | A | 42 min 20 sec | Average | A | 15 sec | Average |
| | B | 33 min 10 sec | 38 min 07 sec | B | 10 sec | 12 sec |
| | C | 38 min 50 sec | | C | 5 sec | |

TABLE 18

Comparison of intranasal retention using saccharin preparation
(The case that the head was set in a vertical direction 30 sec. after, the administration.)

| Spray angle | | Preparation comprising 0.5% saccharin Na of Example 2 | | | 0.5% saccharin Na solution in water | |
|---|---|---|---|---|---|---|
| 65° | A | 35 min 10 sec | Average | A | 55 sec | Average |
| | B | 40 min 55 sec | 38 min 37 sec | B | 15 sec | 27 sec |
| | C | 39 min 45 sec | | C | 10 sec | |
| 90° | A | 42 min 30 sec | Average | A | 5 sec | Average |
| | B | 35 min 45 sec | 40 min 22 sec | B | 10 sec | 7 sec |
| | C | 42 min 50 sec | | C | 5 sec | |

TABLE 19

Comparison of intranasal retention using saccharin preparation
(The case of the administration in lying position on one's back (135°) and holding the position for 5 min)

| Spray angle | | Preparation comprising 0.5% saccharin Na of Example 2 | | | 0.5% saccharin Na solution in water | |
|---|---|---|---|---|---|---|
| 135° | A | 45 min 05 sec | Average | A | 5 sec | Average |
| | B | 29 min 50 sec | 36 min 42 sec | B | 5 sec | 5 sec |
| | C | 35 min 10 sec | | C | 5 sec | |

Hereinafter, some examples that were actually prepared using an active pharmaceutical ingredient are described as a formulation example. But, the present invention should not be limited thereto.

Preparation example 01 (Example 11): Drug formulation applicable to nasal cavity comprising oxymetazoline

| Ingredients | Quantity (%(w/w)) |
|---|---|
| oxymetazoline hydrochloride | 0.05 |
| carboxy vinyl polymer | 0.40 |
| L-arginine | 0.30 |
| benzalkonium chloride | 0.01 |
| purified water | 99.24 |
| Total | 100% |

Adjustment of viscosity: adjusting the viscosity to 1000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 02 (Example 12): Drug formulation applicable to nasal cavity comprising tetrahydrozoline

| Ingredients | Quantity (%(w/w)) |
|---|---|
| tetrahydrozoline hydrochloride | 0.10 |
| chlorpheniramine maleate | 0.50 |

| Preparation example 02 (Example 12): Drug formulation applicable to nasal cavity comprising tetrahydrozoline ||
|---|---|
| Ingredients | Quantity (%(w/w)) |
| lidocaine | 0.30 |
| glycyrrhizinate dipotassium | 0.20 |
| benzethonium chloride | 0.01 |
| carboxy vinyl polymer | 0.55 |
| L-arginine | 0.35 |
| sodium hydroxide | 0.05 |
| macrogol 400 | 3.00 |
| purified water | 94.94 |
| Total | 100% |

Adjustment of viscosity: adjusting the viscosity to 2000 mPa·s by using shearing force, i.e., by rotating the formulation at 20,000 rpm under cooling in an intermittently-jet-stream-generating-type high-speed spinning-type emulsifying device (Type: CLM-0.8S).

| Preparation example 03 (Example 13): Drug formulation applicable to nasal cavity comprising fluticasone propionate ||
|---|---|
| Ingredients | Quantity (%(w/w)) |
| fluticasone propionate | 0.51 |
| carboxy vinyl polymer | 0.53 |
| L-arginine | 0.95 |
| polysorbate 80 | 0.10 |
| concentrated glycerin | 2.00 |
| sodium chloride | 0.125 |
| purified water | 95.785 |
| Total | 100% |

Adjustment of viscosity: adjusting the viscosity to 2200 mPa·s by using shearing force, i.e., by rotating the formulation at 15,000 rpm under cooling in an intermittently-jet-stream-generating-type high-speed spinning-type emulsifying device (Type: CLM-0.8S).

| Preparation example 04 (Example 14): Drug formulation applicable to nasal cavity comprising fluticasone propionate ||
|---|---|
| Ingredients | Quantity (%(w/w)) |
| fluticasone propionate | 0.51 |
| carboxy vinyl polymer | 0.35 |
| gellan gum | 0.15 |
| L-arginine | 0.55 |
| polysorbate 80 | 0.10 |
| concentrated glycerin | 1.00 |
| sodium chloride | 0.25 |
| purified water | 97.09 |
| Total | 100% |

| Preparation example 05 (Example 15): Drug formulation applicable to nasal cavity comprising mometasone furoate ||
|---|---|
| Ingredients | Quantity (%(w/w)) |
| mometasone furoate | 0.50 |
| carboxy vinyl polymer | 0.56 |
| L-arginine | 1.00 |
| polysorbate 80 | 0.10 |
| concentrated glycerin | 2.00 |
| sodium chloride | 0.25 |
| purified water | 95.59 |
| Total | 100% |

Adjustment of viscosity: adjusting the viscosity to 2500 mPa·s by using shearing force, i.e., by rotating the formulation at 15,000 rpm under cooling in an intermittently-jet-stream-generating-type high-speed spinning-type emulsifying device (Type: CLM-0.8S).

| Preparation example 06 (Example 16): Drug formulation applicable to nasal cavity comprising insulin (50 U/g) ||
|---|---|
| Ingredients | Quantity (%(w/w)) |
| insulin | 0.1887 |
| carboxy vinyl polymer | 0.30 |
| L-arginine | 0.55 |
| concentrated glycerin | 1.00 |
| sodium chloride | 0.125 |
| purified water | 97.8363 |
| Total | 100% |

Insulin is mixed in 10 parts of purified water by weight. While, the other ingredients are mixed and the viscosity of the mixture is adjusted by the means as mentioned below, and then the insulin solution is added to the mixture and the resulting mixture is stirred to be uniform.

Adjustment of viscosity: adjusting the viscosity to 750 mPa·s by using shearing force, i.e., by rotating the formulation at 15,000 rpm under cooling in an intermittently-jet-stream-generating-type high-speed spinning-type emulsifying device (Type: CLM-0.8S).

| Preparation example 07 (Example 17): Drug formulation applicable to nasal cavity comprising levocabastine ||
|---|---|
| Ingredients | Quantity (%(w/w)) |
| levocabastine hydrochloride | 0.027 |
| carboxy vinyl polymer | 0.50 |
| L-arginine | 1.05 |
| sucrose fatty acid ester | 0.10 |
| concentrated glycerin | 2.00 |
| sodium chloride | 0.125 |
| purified water | 96.198 |
| Total | 100% |

Adjustment of viscosity: adjusting the viscosity to 2700 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 08 (Example 18): Drug formulation applicable to nasal cavity comprising cromolyn sodium

| Ingredients | Quantity (%(w/w)) |
|---|---|
| cromolyn sodium | 1.00 |
| chlorpheniramine maleate | 0.25 |
| naphazoline hydrochloride | 0.025 |
| carboxy vinyl polymer | 0.65 |
| L-arginine | 0.65 |
| sodium chloride | 0.05 |
| disodium edetate | 0.10 |
| benzalkonium chloride | 0.01 |
| purified water | 97.265 |
| Total | 100% |

Adjustment of viscosity: adjusting the viscosity to 2000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 09 (Example 19): Drug formulation applicable to nasal cavity comprising fentanyl

| Ingredients | Quantity (%(w/w)) |
|---|---|
| fentanyl citrate | 0.157 |
| carboxy vinyl polymer | 0.55 |
| L-arginine | 0.50 |
| polysorbate 80 | 0.10 |
| concentrated glycerin | 1.00 |
| benzalkonium chloride | 0.01 |
| sodium chloride | 0.125 |
| purified water | 97.558 |
| Total | 100% |

Adjustment of viscosity: adjusting the viscosity to 2500 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 10 (Example 20): Drug formulation applicable to nasal cavity comprising fentanyl

| Ingredients | Quantity (%(w/w)) |
|---|---|
| fentanyl citrate | 0.157 |
| carboxy vinyl polymer | 0.175 |
| gellan gum | 0.175 |
| L-arginine | 0.155 |
| polysorbate 80 | 0.10 |
| concentrated glycerin | 1.00 |
| benzalkonium chloride | 0.01 |
| purified water | 98.228 |
| Total | 100% |

Preparation example 11 (Example 21): Drug formulation applicable to nasal cavity comprising fentanyl

| Ingredients | Quantity (%(w/w)) |
|---|---|
| fentanyl citrate | 0.628 |
| carboxy vinyl polymer | 0.55 |
| L-arginine | 0.50 |
| polysorbate 80 | 0.10 |
| concentrated glycerin | 1.00 |
| benzalkonium chloride | 0.01 |
| purified water | 97.212 |
| Total | 100% |

Adjustment of viscosity: adjusting the viscosity to 2500 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 12 (Example 22): Drug formulation applicable to nasal cavity comprising sumatriptan

| Ingredients | Quantity (%(w/w)) |
|---|---|
| sumatriptan | 2.00 |
| carboxy vinyl polymer | 0.50 |
| L-arginine | 0.50 |
| polysorbate 80 | 0.10 |
| concentrated glycerin | 1.00 |
| benzalkonium chloride | 0.01 |
| purified water | 95.89 |
| Total | 100% |

Adjustment of viscosity: adjusting the viscosity to 2500 m·Pas by using shearing force, i.e., by rotating the formulation at 15,000 rpm under cooling in an intermittently-jet-stream-generating-type high-speed spinning-type emulsifying device (Type: CLM-0.8S).

Preparation example 13 (Example 23): Drug formulation applicable to nasal cavity comprising buserelin

| Ingredients | Quantity (%(w/w)) |
|---|---|
| buserelin acetate | 0.1575 |
| carboxy vinyl polymer | 0.50 |
| L-arginine | 0.45 |
| sodium chloride | 0.25 |
| concentrated glycerin | 1.50 |
| benzalkonium chloride | 0.01 |
| purified water | 97.1325 |
| Total | 100% |

Buserelin acetate is mixed in 10 parts of purified water by weight. While, the other ingredients are mixed and the viscosity of the mixture is adjusted by the means as mentioned below, and then the buserelin acetate solution is added to the mixture and the resulting mixture is stirred to be uniform.

Adjustment of viscosity: adjusting the viscosity to 1500 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 14 (Example 24): Drug formulation applicable to nasal cavity comprising desmopressin

| Ingredients | Quantity (%(w/w)) |
|---|---|
| desmopressin acetate | 0.01 |
| carboxy vinyl polymer | 0.50 |
| L-arginine | 0.40 |
| sodium chloride | 0.125 |
| concentrated glycerin | 1.50 |
| benzalkonium chloride | 0.01 |
| purified water | 97.455 |
| Total | 100% |

Desmopressin acetate is mixed in 10 parts of purified water by weight. While, the other ingredients are mixed and the viscosity of the mixture is adjusted by the means as mentioned below, and then the desmopressin acetate solution is added to the mixture and the resulting mixture is stirred to be uniform.

Adjustment of viscosity: adjusting the viscosity to 2000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 15 (Example 25): Drug formulation applicable to skin comprising loxoprofen sodium

| Ingredients | Quantity (%(w/w)) |
|---|---|
| loxoprofen sodium | 1.134 |
| carboxy vinyl polymer | 1.00 |
| triethanolamine | 1.30 |
| ethanol | 20.00 |
| 1,3-butylene glycol | 5.00 |
| purified water | 71.566 |
| Total | 100% |

Adjustment of viscosity: adjusting the viscosity to 3500 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 16 (Example 26): Drug formulation applicable to skin comprising loxoprofen sodium

| Ingredients | Quantity (%(w/w)) |
|---|---|
| loxoprofen sodium | 1.134 |
| N-methyl-2-pyrrolidone | 2.50 |
| carboxy vinyl polymer | 1.00 |
| octyldodecanol | 10.00 |
| polyoxyl 40 stearate | 1.00 |
| glyceryl monostearate | 1.00 |
| sodium hydroxide | 0.40 |
| 1,3-butylene glycol | 5.00 |
| purified water | 77.966 |
| Total | 100% |

Adjustment of viscosity: adjusting the viscosity to 3000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 17 (Example 27): Drug formulation applicable to skin comprising chlorpheniramine maleate

| Ingredients | Quantity (%(w/w)) |
|---|---|
| chlorpheniramine maleate | 1.00 |
| lidocaine | 0.50 |
| l-menthol | 5.00 |
| dl-camphor | 2.00 |
| carboxy vinyl polymer | 1.20 |
| triethanolamine | 1.68 |
| ethanol | 50.00 |
| 1,3-butylene glycol | 10.00 |
| purified water | 28.62 |
| Total | 100% |

Adjustment of viscosity: adjusting the viscosity to 5000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 18 (Example 28): Drug formulation applicable to skin comprising acyclovir

| Ingredients | Quantity (%(w/w)) |
|---|---|
| acyclovir | 5.00 |
| polysorbate 80 | 1.00 |
| carboxy vinyl polymer | 1.20 |
| octyldodecanol | 5.00 |
| polyoxyl 40 stearate | 0.50 |
| glyceryl monostearate | 0.50 |
| L-arginine | 0.75 |
| 1,3-butylene glycol | 5.00 |
| purified water | 81.05 |
| Total | 100% |

Adjustment of viscosity: adjusting the viscosity to 2500 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 19 (Example 29): Drug formulation applicable to skin comprising lidocaine

| Ingredients | Quantity (%(w/w)) |
|---|---|
| lidocaine | 7.00 |
| carboxy vinyl polymer | 1.20 |
| octyldodecanol | 10.00 |
| polyoxyl 40 stearate | 1.00 |
| glyceryl monostearate | 1.00 |
| sodium hydroxide | 0.48 |
| 1,3-butylene glycol | 5.00 |
| purified water | 74.32 |
| Total | 100% |

Adjustment of viscosity: adjusting the viscosity to 3500 mPa·s by using shearing force, i.e., by rotating the formulation-at 15,000 rpm under cooling in an intermittently-jet-stream-generating-type high-speed spinning-type emulsifying device (Type: CLM-0.8S).

Preparation example 20 (Example 30): Drug formulation applicable to skin comprising terbinafine

| Ingredients | Quantity (%(w/w)) |
|---|---|
| terbinafine hydrochloride | 1.00 |
| crotamiton | 5.00 |
| carboxy vinyl polymer | 0.60 |
| octyldodecanol | 5.00 |
| polyoxyl 40 stearate | 0.50 |
| glyceryl monostearate | 0.50 |
| sodium hydroxide | 0.40 |
| 1,3-butylene glycol | 5.00 |
| purified water | 82.00 |
| Total | 100% |

Adjustment of viscosity: adjusting the viscosity to 3000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 21 (Example 31): Drug formulation applicable to skin comprising lanoconazole

| Ingredients | Quantity (%(w/w)) |
|---|---|
| lanoconazole | 1.0 |
| crotamiton | 5.0 |
| polyoxyethylene hydrogenated castor oil 40 | 1.0 |
| carboxy vinyl polymer | 1.0 |
| triethanolamine | 1.0 |
| ethanol | 55.0 |
| 1,3-butylene glycol | 10.0 |
| purified water | 26.0 |
| Total | 100% |

Adjustment of viscosity: adjusting the viscosity to 3000 mPa·s by using shearing force, i.e., by rotating the formulation at 10,000 rpm under cooling in an intermittently-jet-stream-generating-type high-speed spinning-type emulsifying device (Type: CLM-0.8S).

Preparation example 22 (Example 32): Drug formulation applicable to skin comprising lanoconazole

| Ingredients | Quantity (%(w/w)) |
|---|---|
| lanoconazole | 1.00 |
| crotamiton | 5.00 |
| carboxy vinyl polymer | 1.00 |
| octyldodecanol | 10.00 |
| polyoxyl 40 stearate | 0.50 |
| glyceryl monostearate | 0.50 |
| sodium hydroxide | 0.40 |
| 1,3-butylene glycol | 5.00 |
| purified water | 76.60 |
| Total | 100% |

Adjustment of viscosity: adjusting the viscosity to 3500 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 23 (Example 33): Drug formulation applicable to skin comprising betamethasone butyrate propionate

| Ingredients | Quantity (%(w/w)) |
|---|---|
| betamethasone butyrate propionate | 0.05 |
| crotamiton | 5.00 |
| carboxy vinyl polymer | 1.00 |
| octyldodecanol | 10.00 |
| macrogol 400 | 5.00 |
| polyoxylpolyoxyl 45 stearate | 0.50 |
| glyceryl monostearate | 0.50 |
| sodium hydroxide | 0.25 |
| disodium edetate | 0.01 |
| purified water | 77.69 |
| Total | 100% |

Adjustment of viscosity: adjusting the viscosity to 4500 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 24 (Example 34): Drug formulation applicable to skin comprising maxacalcitol

| Ingredients | Quantity (%(w/w)) |
|---|---|
| maxacalcitol | 0.0025 |
| carboxy vinyl polymer | 0.85 |
| octyldodecanol | 10.00 |
| concentrated glycerin | 5.00 |
| polyoxyl 45 stearate | 0.50 |
| glyceryl monostearate | 0.50 |
| sodium hydroxide | 0.25 |
| disodium edetate | 0.005 |
| purified water | 82.8925 |
| Total | 100% |

Adjustment of viscosity: adjusting the viscosity to 3000 m·Pas by using shearing force, i.e., by rotating the formulation at 20,000 rpm under cooling in an intermittently-jet-stream-generating-type high-speed spinning-type emulsifying device (Type: CLM-0.8S).

Preparation example 25 (Example 35): Drug formulation applicable to the surround of anus comprising prednisolone

| Ingredients | Quantity (%(w/w)) |
|---|---|
| prednisolone acetate | 0.10 |
| dibucaine | 0.50 |
| benzalkonium chloride | 0.10 |
| l-menthol | 0.10 |
| polysorbate 80 | 1.00 |
| carboxy vinyl polymer | 0.95 |
| L-arginine | 0.35 |
| disodium edetate | 0.05 |
| purified water | 96.85 |
| Total | 100% |

Adjustment of viscosity: adjusting the viscosity to 4000 mPa·s by using shearing force, i.e., by rotating the formulation at 15,000, rpm under cooling in an intermittently-jet-stream-generating-type high-speed spinning-type emulsifying device (Type: CLM-0.8S).

Preparation example 26 (Example 36): Drug formulation applicable to the surround of anus comprising diflucortolone valerate

| Ingredients | Quantity (%(w/w)) |
|---|---|
| diflucortolone valerate | 0.01 |
| lidocaine | 2.00 |
| carboxy vinyl polymer | 0.85 |
| L-arginine | 0.55 |
| octyldodecanol | 5.00 |
| polysorbate 80 | 1.00 |
| polyoxyl 45 stearate | 1.00 |
| glyceryl monostearate | 1.00 |
| purified water | 88.59 |
| Total | 100% |

Adjustment of viscosity: adjusting the viscosity to 3000 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 27 (Example 37): Drug formulation applicable to scalp comprising minoxidil

| Ingredients | Quantity (%(w/w)) |
|---|---|
| minoxidil | 1.00 |
| carboxy vinyl polymer | 0.50 |
| triethanolamine | 0.50 |
| ethanol | 55.00 |
| 1,3-butylene glycol | 10.00 |
| purified water | 33.00 |
| Total | 100% |

Adjustment of viscosity: adjusting the viscosity to 4000 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 28 (Example 38): Drug formulation for ophthalmic application comprising ketotifen

| Ingredients | Quantity (%(w/w)) |
|---|---|
| ketotifen fumarate | 0.069 |
| polysorbate 80 | 0.005 |
| carboxy vinyl polymer | 0.25 |
| L-arginine | 0.20 |
| concentrated glycerin | 1.00 |
| disodium edetate | 0.005 |
| benzalkonium chloride | 0.005 |
| purified water | 98.466 |
| Total | 100% |

Adjustment of viscosity: adjusting the viscosity to 100 mPa·s by using shearing force, i.e., by rotating the formulation at 15,000 rpm under cooling in an intermittently-jet-stream-generating-type high-speed spinning-type emulsifying device (Type: CLM-0.8S).

Preparation example 29 (Example 39): Drug formulation for oral application comprising triamcinolone acetonide

| Ingredients | Quantity (%(w/w)) |
|---|---|
| triamcinolone acetonide | 0.025 |
| polysorbate 80 | 0.050 |
| carboxy vinyl polymer | 0.50 |
| L-arginine | 0.45 |
| concentrated glycerin | 1.00 |
| disodium edetate | 0.01 |
| benzalkonium chloride | 0.01 |
| purified water | 97.955 |
| Total | 100% |

Adjustment of viscosity: adjusting the viscosity to 4000 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 30 (Example 40): Veterinary drug formulation applicable to body comprising orbifloxacin

| Ingredients | Quantity (%(w/w)) |
|---|---|
| orbifloxacin | 1.00 |
| miconazole nitrate | 1.00 |
| triamcinolone acetonide | 0.10 |
| crotamiton | 5.00 |
| concentrated glycerin | 5.00 |
| carboxy vinyl polymer | 0.64 |
| octyldodecanol | 10.00 |
| polyoxyl 45 stearate | 0.50 |
| glyceryl monostearate | 0.50 |
| sodium hydroxide | 0.10 |
| disodium edetate | 0.005 |
| purified water | 76.155 |
| Total | 100% |

Adjustment of viscosity: adjusting the viscosity to 5000 mPa·s by using shearing force, i.e., by rotating the formulation at 20,000 rpm under cooling in an intermittently-jet-stream-generating-type high-speed spinning-type emulsifying device (Type: CLM-0.8S).

Preparation example 31 (Example 41): Veterinary drug formulation applicable to ear comprising orbifloxacin

| Ingredients | Quantity (%(w/w)) |
|---|---|
| orbifloxacin | 1.00 |
| miconazole nitrate | 1.00 |
| crotamiton | 5.00 |
| concentrated glycerin | 5.00 |
| carboxy vinyl polymer | 0.55 |
| octyldodecanol | 10.00 |
| polyoxyl 45 stearate | 0.50 |
| glyceryl monostearate | 0.50 |
| sodium hydroxide | 0.086 |
| disodium edetate | 0.005 |
| purified water | 76.359 |
| Total | 100% |

Adjustment of viscosity: adjusting the viscosity to 500 mPa·s by using shearing force, i.e., by rotating the formulation at 20,000 rpm under cooling in an intermittently-jet-stream-generating-type high-speed spinning-type emulsifying device (Type: CLM-0.8S).

Industrial Applicability

As mentioned above, the sprayable gel-type skin/mucosa-adhesive preparation of the invention is improved in the retention, compared with a conventional liquid formulation, and further using an upper-pressure-relief airless-type spray container which is different from a conventional container wherein a liquid formulation is pumped up through a tube, and it has also become possible to prepare a preparation suitable for the gel-type formulation. Especially, when using it in a nasal spray, it has become possible to carry out a administration by means of a nasal spray in an angle of 45° or more in which it had been impossible to be sprayed until now.

Furthermore, in an upper-pressure-relief airless-type spray container, the present inventors has improved a body of slidable valve in the container to prepare a spray container characterized in that the residual rate is low, and the sprayed amount is stable. Thereby it has become possible to prepare a sprayable gel-type skin/mucosa-adhesive preparation which is safe and economy on the cost.

Therefore, when using the sprayable gel-type skin/mucosa-adhesive preparation of the invention and the administration system comprising the preparation, the absorption and clearance in the treatment of rhinitis or other disease has been improved, and it is possible to spray in an angle suitable for the use, furthermore it is possible to almost use up while keeping a constant amount of one spray shot to the end. Therefore, the present invention has enabled a more effective and useful preparation for nasal spray. In addition, the present invention is expected to become a very useful administration system in the research and development of drug preparation for intranasal administration which is a drug administration route for systemic action.

The invention claimed is:

1. A sprayable gel-type skin/mucosa-adhesive preparation that takes a particle form after spraying, comprising a gel formulation, which contains an active pharmaceutical ingredient in a gel base material comprising a skin/mucosa-adhesive agent,
    wherein the skin/mucosa-adhesive agent comprises a carboxy vinyl polymer,
    the skin/mucosa-adhesive agent is treated with an outside shearing force that adjusts viscosity of the skin/mucosa-adhesive agent to be in the range of 50 mPa·s to 5000 mPa·s, and
    a particle of the sprayed formulation has a viscosity retention rate of about 100%.

2. The sprayable gel-type skin/mucosa-adhesive preparation set forth in claim 1, wherein the mucosa to which the preparation is applied is a mucosa of a nasal cavity, an eye, an ear, an oral cavity, a rectum, a vagina, or an urethra; or the skin to which the preparation is applied is skin of a hand, a finger, a leg, a body, a groin, a scalp, surroundings of an anus, or surroundings of a genitalium.

3. The sprayable gel-type skin/mucosa-adhesive preparation set forth in claim 1, wherein the mucosa to which the preparation is applied is a mucosa of a nasal cavity.

4. The sprayable gel-type skin/mucosa-adhesive preparation set forth in claim 1, wherein the skin/mucosa-adhesive agent contains the carboxy vinyl polymer in an amount of 0.1% (w/w) to 2.0% (w/w).

5. The sprayable gel-type skin/mucosa-adhesive preparation set forth in claim 1, wherein the skin/mucosa-adhesive agent contains the carboxy vinyl polymer and gellan gum in a total amount of 0.2% (w/w) to 4.0% (w/w).

6. The sprayable gel-type skin/mucosa-adhesive preparation set forth in claim 4,
    wherein the skin/mucosa-adhesive agent further comprises a viscosity modulating agent that adjusts the viscosity of the skin/mucosa-adhesive agent 7. The sprayable gel-type skin/mucosa-adhesive preparation set forth in claim 6, wherein the viscosity modulating agent is selected from a group consisting of sodium chloride, potassium chloride and calcium chloride.

8. The sprayable gel-type skin/mucosa-adhesive preparation set forth in claim 1, further comprising a thickening agent for the carboxy vinyl polymer, which is selected from the group consisting of a neutral amino acid or basic water-soluble amino acid and is contained in a ratio of 1: 0.5 to 1: 3 relative to the carboxy vinyl polymer by weight.

9. The sprayable gel-type skin/mucosa-adhesive preparation set forth in claim 8, wherein the thickening agent is at least one material selected from the group consisting of arginine, lysine, and ornithine.

10. The sprayable gel-type skin/mucosa-adhesive preparation set forth in claim 1, wherein the gel formulation contains an active pharmaceutical ingredient in an amount of 0.001-10% (w/w) in the gel formulation.

11. The sprayable gel-type skin/mucosa-adhesive preparation set forth in claim 1, wherein the active pharmaceutical ingredient is in a dissolved state.

12. The sprayable gel-type skin/mucosa-adhesive preparation set forth in claim 1, wherein the skin/mucosa-adhesive agent further comprises gellan gum.

* * * * *

UNITED STATES PATENT AND TRADEMARK OFFICE
CERTIFICATE OF CORRECTION

| | |
|---|---|
| PATENT NO. | : 8,771,711 B2 |
| APPLICATION NO. | : 12/226287 |
| DATED | : July 8, 2014 |
| INVENTOR(S) | : Kamishita |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this
Fifteenth Day of December, 2015

Michelle K. Lee
*Director of the United States Patent and Trademark Office*